US010182746B1

(12) United States Patent
Demiralp et al.

(10) Patent No.: US 10,182,746 B1
(45) Date of Patent: Jan. 22, 2019

(54) DECOUPLING BODY MOVEMENT FEATURES FROM SENSOR LOCATION

(71) Applicant: Verily Life Sciences LLC, Mountain View, CA (US)

(72) Inventors: Emre Demiralp, San Francisco, CA (US); Hongsheng Wang, Sunnyvale, CA (US); Philip Stephens, Morgan Hill, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 34 days.

(21) Appl. No.: 15/659,183

(22) Filed: Jul. 25, 2017

(51) Int. Cl.
*A61B 5/11* (2006.01)
*A61B 5/00* (2006.01)
*G06K 9/00* (2006.01)
*A63B 24/00* (2006.01)

(52) U.S. Cl.
CPC .......... *A61B 5/1118* (2013.01); *A61B 5/6802* (2013.01); *A61B 5/721* (2013.01); *A63B 24/0003* (2013.01); *A63B 24/0021* (2013.01); *A63B 24/0062* (2013.01); *G06K 9/00342* (2013.01)

(58) Field of Classification Search
None
See application file for complete search history.

(56) References Cited

U.S. PATENT DOCUMENTS

| 8,165,844 B2 | 4/2012 | Luinge et al. |
| 2015/0164377 A1 | 6/2015 | Vaidhi et al. |
| 2016/0100776 A1* | 4/2016 | Najafi ................ A61B 5/1116 600/595 |
| 2016/0324447 A1* | 11/2016 | Hallberg ............. A61B 5/1122 |

* cited by examiner

*Primary Examiner* — Devin Henson
*Assistant Examiner* — Benjamin Melhus
(74) *Attorney, Agent, or Firm* — Kilpatrick Townsend & Stockton LLP

(57) ABSTRACT

Systems and techniques are disclosed for decoupling a wearable sensor's location on a user from the body movements desired to be measured by the sensor. Sensor data can be dynamically analyzed to determine a reference event (e.g., a static pose), which can be used to generate or update a transformation parameter (e.g., a quaternion or a rotational matrix). The transformation parameter can be applied to sensor data to transform the sensor data from the sensor's frame of reference to a global frame of reference. Once transformed, the movement data in the global frame can be analyzed to identify sensor-location-agnostic biomechanical features (e.g., body movements or movement trends), which can be further analyzed to identify probable or potential diagnoses correlated with the identified biomechanical features.

26 Claims, 11 Drawing Sheets

DECOUPLING BODY MOVEMENT FEATURES FROM SENSOR LOCATION

TECHNICAL FIELD

The present disclosure relates to using sensors to detect body movements generally and more specifically to collecting and processing sensor data, such as from a wearable sensor.

BACKGROUND

Sensors, such as motion sensors within wearable devices, are becoming ever more prevalent to collect and detect data about a user. Detected data can be used for many purposes, such as research, medical monitoring, motion capture, or other purposes. Sensors can be incorporated into various different wearable devices. For example, inertial measurement units (IMUs) can be incorporated in many wearable devices, such as watches, trackers, phones, and the like. IMUs can provide accelerometer, magnetometer, and/or gyroscope sensor data.

Wearable sensors bring the convenience of staying with the user during movement, however placement of wearables sensors can significantly affect the accuracy and reliability of the any inferences made from the raw sensor data. For example, a user performing an action can generate extremely different sensor data in a foot-worn sensor and an arm-worn sensor. Further, the number of degrees of freedom of movement vary between different locations on a user. Therefore, in order to provide a wearable device capable of accurately making inferences about a user's movements, the wearable device can be designed to be used at a specific location on a user. For example, certain wrist-worn step counting devices may contain algorithms capable of relatively accurately estimating step counts based on sensor data from wrist movements, however the same devices would provide inaccurate and unreliable estimates if the same device were carried in a pocket or backpack.

In many cases, however, users may decide to not wear a particular wearable device at its intended location or at all due to comfort issues, cosmetic issues, or other issues. For example, a user prescribed to wear a chest strap for medical monitoring may end up forgetting to put it on or intentionally decide to not put it on due to discomfort. Therefore, it can be desirable to provide a wearable device capable of making accurate and reliable inferences about a user's movements while permitting the wearable device to be placed or worn at desirable locations.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present invention include systems, comprising one or more data processors and a non-transitory computer-readable storage medium containing instructions which, when executed on the one or more data processors, cause the one or more data processors to perform operations including: receiving sensor data in a sensor frame, wherein the sensor data is indicative of movement of a wearable device; automatically identifying a reference event using at least a portion of the sensor data; determining a reference sensor orientation at the reference event using at least the portion of the sensor data, wherein the reference sensor orientation is associated with an orientation of the wearable device in a global frame; calculating a transformation parameter using the reference sensor orientation and the sensor data, wherein the transformation parameter includes a quaternion or a rotational matrix; transforming the sensor data using the transformation parameter to generate movement data, wherein the movement data is associated with movement of the wearable device in the global frame; and determining a sensor-location-agnostic biomechanical feature using the movement data.

Embodiments of the present invention include a computer-implemented method, comprising: receiving sensor data in a sensor frame, wherein the sensor data is indicative of movement of a wearable device; automatically identifying a reference event using at least a portion of the sensor data; determining a reference sensor orientation at the reference event using at least the portion of the sensor data, wherein the reference sensor orientation is associated with an orientation of the wearable device in a global frame; calculating a transformation parameter using the reference sensor orientation and the sensor data, wherein the transformation parameter includes a quaternion or a rotational matrix; transforming the sensor data using the transformation parameter to generate movement data, wherein the movement data is associated with movement of the wearable device in the global frame; and determining a sensor-location-agnostic biomechanical feature using the movement data.

Embodiments of the present invention include a computer-program product tangibly embodied in a non-transitory machine-readable storage medium, including instructions configured to cause a data processing apparatus to perform operations including: receiving sensor data in a sensor frame, wherein the sensor data is indicative of movement of a wearable device; automatically identifying a reference event using at least a portion of the sensor data; determining a reference sensor orientation at the reference event using at least the portion of the sensor data, wherein the reference sensor orientation is associated with an orientation of the wearable device in a global frame; calculating a transformation parameter using the reference sensor orientation and the sensor data, wherein the transformation parameter includes a quaternion or a rotational matrix; transforming the sensor data using the transformation parameter to generate movement data, wherein the movement data is associated with movement of the wearable device in the global frame; and determining a sensor-location-agnostic biomechanical feature using the movement data.

In some cases, the sensor-location-agnostic biomechanical feature is associated with movement of a body part at which the wearable device is not positioned. In some cases, the method or operations further comprise: receiving supplemental sensor data associated with continued movement of the wearable device in the sensor frame; transforming the supplemental sensor data using the transformation parameter to generate supplemental movement data, wherein the supplemental movement data is associated with continued movement of the wearable device in the global frame; and determining the sensor-location-agnostic biomechanical feature using the movement data. In some cases, the method or operations further comprise: automatically identifying a supplemental reference event using at least some of the supplemental sensor data; determining a supplemental reference sensor orientation at the supplemental reference event using at least the portion of the supplemental sensor data, wherein the supplemental reference sensor orientation is associated with a supplemental orientation of the wearable device in the global frame; and updating the transformation parameter using the supplemental reference sensor orientation and the supplemental sensor data, wherein transforming the supplemental sensor data using the transformation parameter to generate supplemental movement data includes using the updated transformation parameter. In some cases, the method or operations further comprise: determining that the wearable device is being worn again after being removed from an original location; receiving new sensor data associated with movement of the wearable device in a new sensor frame, wherein the new sensor data is associated with movement of the wearable device being worn at a new location that is different from the original location; automatically identifying a new reference event using at least a portion of the new sensor data; determining a new reference sensor orientation at the new reference event using at least the portion of the new sensor data, wherein the new reference sensor orientation is associated with the orientation of the wearable device in the global frame; calculating a new transformation parameter using the new reference sensor orientation and the new sensor data, wherein the new transformation parameter includes a quaternion or a rotational matrix; transforming the new sensor data using the new transformation parameter to generate new movement data, wherein the new movement data is associated with movement of the wearable device in the global frame; and determining the sensor-location-agnostic biomechanical feature using the new movement data. In some cases, the method or operations further comprise generating a diagnosis inference using the sensor-location-agnostic biomechanical feature. In some cases, the method or operations further comprise receiving second movement data associated with movement of a second wearable device in the global frame, wherein the second wearable device is spaced apart from the wearable device, and wherein inferring the sensor-location-agnostic biomechanical feature includes using the movement data and the second movement data. In some cases, determining the sensor-location-agnostic biomechanical feature includes calculating a velocity of the sensor in the global frame using the re-oriented movement data; detecting an occurrence of a zero-expected-velocity event using the sensor data; calculating an offset between zero and the calculated velocity when the zero-expected-velocity event occurs; and correcting the calculated velocity using the offset.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
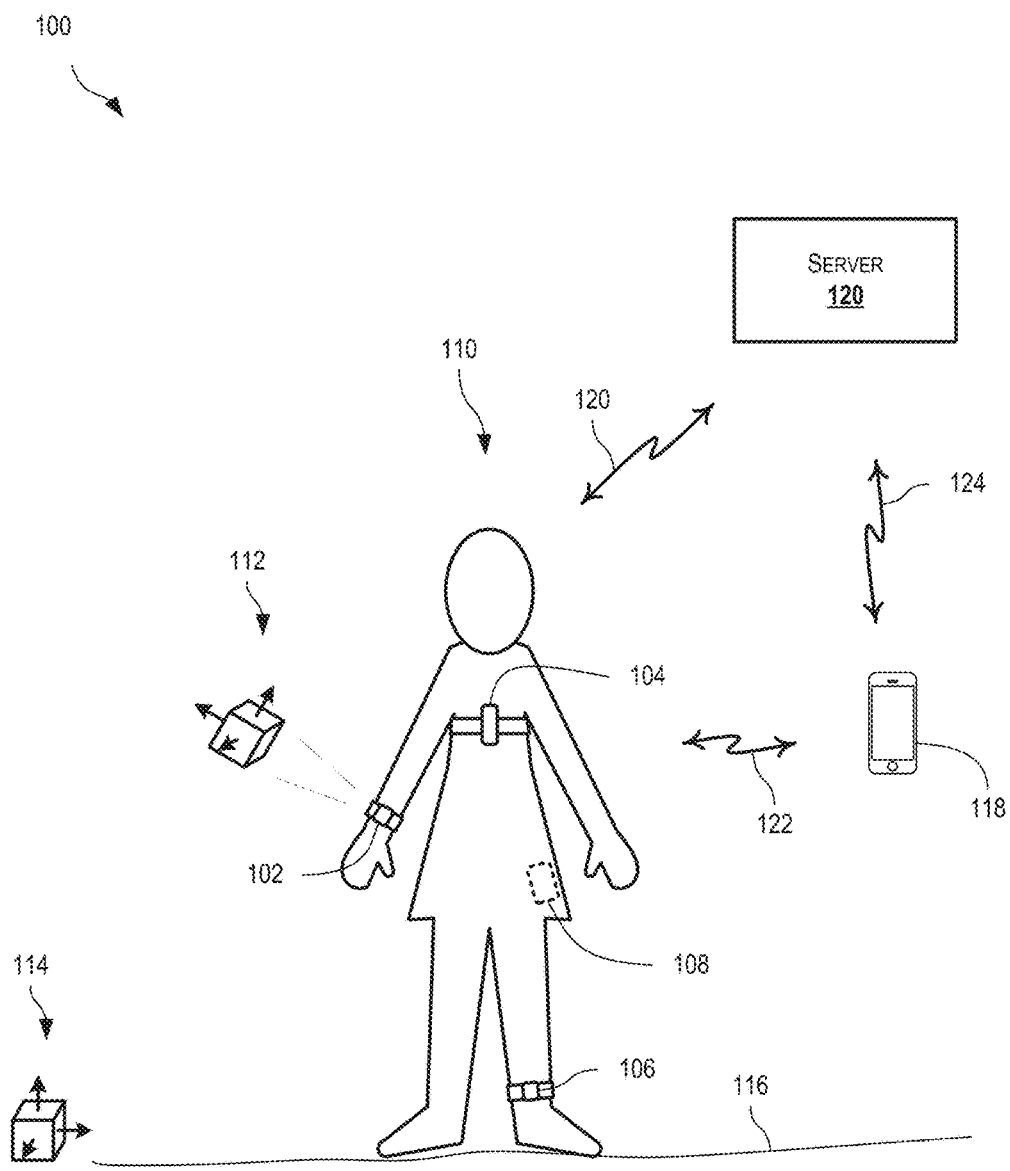
FIG. 1 is schematic diagram depicting a system for detecting biomechanical features according to certain aspects of the present disclosure.

Certain aspects and features of the present disclosure relate to systems and techniques for decoupling a wearable sensor's location from the body movements desired to be measured or otherwise detected by the sensor. Certain biomechanical features, such as body movements or body movement trends, can be detected using a wearable sensor regardless of the wearable sensor's location on the user. These sensor-location-agnostic biomechanical features can be measured, detected, and/or otherwise inferred from sensor data irrespective of the placement of the sensor on the user, through transformation of the sensor data (e.g., data collected in the sensor's frame of reference) into movement data in a global frame of reference. Sensor data can be analyzed to determine a reference event (e.g., a static pose), which can be used to generate a transformation parameter (e.g., a quaternion or a rotational matrix). The transformation parameter at past, current, and/or future time points can be inferred by iteratively updating from the reference pose, and can be used to transform the sensor data from the sensor's frame of reference to a global frame of reference. Once transformed, the movement data in the global frame of reference can be analyzed to identify biomechanical features. Identified biomechanical features can be further analyzed to identify probable or potential diagnoses correlated with the identified biomechanical features. In some cases, continuing sensor data can be dynamically analyzed to identify additional reference events so as to update the transformation parameter.

As used herein, the term wearable sensor can include any suitable sensor supportable by a user during movement of the user. In some cases, a sensor can be a device that includes some combination of acceleration, gyroscopic, and/or magnetic sensors, such as an inertial measurement unit (IMU). In some cases, the sensor can be integrated into a wearable device that performs other functions as well, such as a watch, phone, camera, bodyworn electrocardiogram machine, or the like. In some cases, the sensor can be removably attached to the user (e.g., a watch on a watchband), can be carried directly by a user (e.g., a phone carried in the hand), can be indirectly carried by the user (e.g., a phone carried in a backpack supported by the user), or can be permanently or semi-permanently attached to the user (e.g., an IMU within a medical implant, such as a pacemaker). The wearable sensor can be capable of generating and transmitting sensor data associated with movement of the sensor with respect to its own frame of reference (e.g., sensor frame).

In some cases, a wearable sensor can include one or more wearable sensor targets designed to be read by a separate receiver, which need not be wearable. For example, sensor targets can include reflective or illuminated targets detectable by a video capture device, such as a camera. Detection of the movement of the one or more sensor targets can provide intermediate sensor data associated with movement of the sensor target(s) with respect to the video capture device's frame of reference (e.g., detector frame). Knowledge of the video capture device's movements, or lack thereof, can be used to translate the sensor target(s) movements in the detector frame to movements in the sensor target(s)' frame of reference (e.g., sensor frame).

Certain aspects and feature of the present disclosure are especially useful in the field of healthcare. Many medical systems around the world are progressing towards a value-based care approach where physicians and healthcare systems are reimbursed and evaluated based on the value they provide for patients rather than number of individual services. This paradigm requires detailed measurement of multiple aspects of a patient's health. Detection and monitoring of biomechanical features (e.g., body movement features) from a wearable device can be used to predict, monitor, and analyze disease and disability states. In some cases, these biomechanical features can be used to digitally phenotype patients with conditions or symptoms, such as movement disorders like Parkinson's Disease, Essential Tremor, Alzheimer's Disease, Mental Health, Cardiovascular disease, and the like. However, monitoring of the movement of a particular body part is traditionally tied to a wearable sensor located on that particular body part desired to be monitored. Thus, monitor movement of multiple body parts may require a patient to wear multiple sensor devices, which can be encumbering, uncomfortable, unsightly, and may be otherwise undesirable or difficult. In some cases, the presence of the multiple sensor devices may undesirably affect the measurements being taken, such as a sensor device directly or indirectly inhibits the body movement desired to be monitored.

Certain aspects and features of the present disclosure relate to algorithms that decouple biomechanical features characterizing a patient's body movements from the locations of the sensors responsible for performing the measurements. Often, a biomechanical feature desired to be monitored can be relatively stable for a particular individual performing a particular activity over time. Expected variations of the biomechanical feature can be limited to a threshold range, outside of which may be indicative of a change in the individual's health.

Certain aspects and features of the present disclosure relate to a computing device that can transform sensor data from a local, sensor frame to a global frame (e.g., an earth frame). In some cases, a biomechanical modeling system can then compute sensor-location-agnostic biomechanical features based on the global frame movement data.

In a simplified example, a user may be walking on a floor with an ankle-worn sensor. The user may be oriented such that walking forward reflects positive movement in an $X_{global}$ direction, sidestepping to the right reflects positive movement in the $Y_{global}$ axis, and jumping reflects positive movement in the $Z_{global}$ axis. The ankle-worn sensor may be placed on a user with its $X_{sensor}$ axis facing up the user's leg, its $Y_{sensor}$ axis facing towards the user's toes, and its $Z_{sensor}$ axis facing away from the user's ankle. During normal walking, the sensor may record slight pulsatile movement in the $X_{sensor}$ axis, substantial pulsatile movement in the $Y_{sensor}$ axis, and little to no movement in the $Z_{sensor}$ axis. After transforming to a global frame, this same sensor data can be stored as movement data representing substantial pulsatile movement in the $X_{global}$ direction (e.g., attributable to swinging the foot forwards), little or no movement in the $Y_{global}$ direction (e.g., attributable to not swinging the foot outwards during normal walking), and slight pulsatile movement in the $Z_{global}$ direction (e.g., attributable to raising and lowering the foot while walking). In this example, if the placement and orientation of the sensor is always known, transformation to the global frame may be simplified to noise filtering and direct conversions (e.g., $X_{sensor}=Z_{global}$). However, if the sensor is moved to a different or unknown placement or orientation, transformation of the sensor data may be nontrivial. In some cases, different geometries (e.g., non-Euclidean) and geometrical descriptions can be used to describe a frame of reference other than X, Y, and Z axes.

Certain aspects and features of the present disclosure are suitable for automatically and dynamically generating and updating transformation parameters regardless of the placement and orientation of the sensor. For example, certain patterns detected in the sensor data can correlate to a heel strike event, followed by a stance phase, followed by a toe off event. Once this reference event is detected, it can be determined that the sensor is located on an ankle and that at the time of the stance phase, the foot to which that ankle is attached is stationary and resting on the ground. Thus, the sensor data at that time can be used, along with the knowledge of the reference event, to determine a transformation parameter capable of transforming sensor data in the sensor frame into movement data in the global frame. In some cases, the same transformation parameter can be iteratively updated (e.g., by incorporating real-time IMU readings using a Kalman filter, as described herein) and used to transform additional sensor data. In some cases, detection of additional reference events can be used to further refine or update the transformation parameter. Reference events can be any event that is detectable through sensor data in the sensor's frame of reference and that can be associated with a position and/or orientation of the sensor in global frame. Once movement data is available in a global frame, the movement data can be used for additional purposes, such as to measure movement of the body part to which the sensor is attached, to determine movement of other body parts to which the sensor is not attached, to determine general movement of the body incorporating the body part to which the sensor is attached, or to determine other biomechanical features.

In some cases, a computing device can compute statistical and/or machine learned correlations between sensor data from sensors worn on various different parts of the body. Based on the computed correlations, a biomechanical modeling system can compute sensor-location-agnostic biomechanical features pertaining to various body movements based on sensor data of wearable sensors.

Using certain aspects and features of the present disclosure, a biomechanical feature characterizing movement of a body part can be derived from at least one sensor worn at a location different from the location of the body part. The biomechanical modeling system can then model the well-being of a patient based on the sensor-location-agnostic biomechanical features.

In some cases, certain aspects and features of the present disclosure are especially suitable for sensor-location-agnostic detection and measuring of an individual's turning movements (e.g., clockwise or counterclockwise turning while stationary or while moving). Monitoring an individual's turning movements can help predict or diagnose certain health risks. It has been determined that individuals at more advanced stages of the disease tend to make shallower turn angles and tend to turn at lower turn speeds when making directional changes, as compared to individuals at earlier stages of the disease. This data suggests that monitoring these types of turn features of patients in daily living may provide important insights to the disease prognosis. Using existing technology, a wearable device would generally need to be secured to a body part having a high correlation with the biomechanical feature, such as a lower limb or torso in the case of detecting turn angles. Existing technology has been unable to successfully or efficiently overcome the challenges associated with inopportune placement of the sensor, such as on a wrist-worn device. A wrist-worn device can be susceptible to the extra degrees of freedom and large range of motion of the arm during activities of daily living. Additionally, there are large variances in arm swing patterns between different populations and in some cases between different arms of an individual. In some cases, variances between different arms of an individual can be related to a medical condition (e.g., stroke) or simply the eccentricities of the individual's professional or daily life. Further, the sensor data collected while a user is turning can vary greatly depending on which arm is being used and upon how the sensor is oriented on the arm.

However, certain aspects and features of the present disclosure can be used to obtain this turning data with a sensor placed in any suitable location, such as a wrist-worn sensor or a sensor placed in a backpack carried by the individual. Limitations, such as those described above with respect to traditional wrist-worn sensors, can be overcome by using the techniques described herein to translate the sensor data from the local, sensor frame of reference to movement data in a global frame of reference. When attempted using certain aspects and features of the present disclosure, accurate and reliable turn detection was made from various sensors located at various positions and orientations on a user's body. In an example, sensor data from a left wrist sensor frame and sensor data from a right wrist sensor frame were both collected during a walking and turning exercise, as well as data from other sensors. Both sets of wrist sensor data were different in their respective sensor frames, as expected due to the different placements and orientations of the sensors. However, once both sets of wrist sensor data were translated to the global frame using systems and techniques described herein, the resultant sets of movement data were similar and nearly identical. Thus, the desired biomechanical features (e.g., turning data) was easily discernable using either set of movement data in the global frame, despite the difference in location and orientation of the sensors.

In some cases, additional filter can be used to improve sensor data or movement data. For example, a wavelet denoise process (e.g., discrete wavelet transformation and kernel smoother) can be used to remove noise from movement data when necessary.

Certain aspects and features of the present disclosure enable sensors to be placed in more convenient locations than otherwise. Additionally, the availability of more convenient locations can improve patient compliance. Further, the ability to decouple sensor location from the biomechanical feature being detected can facilitate existing devices to be used for new purposes, such as using the sensors in an existing smartphone to help monitor the severity of multiple sclerosis, as mentioned above.

Certain aspects and features of the present disclosure enable data processing devices to more efficiently and/or effectively process biometric data. Rather than processing sensor data (e.g., in a sensor frame of reference), the data processing device can simply process movement data (e.g., in a global frame of reference). Therefore, the same data processing apparatus can be used despite the location of the sensor. In some cases, the translation to a global frame of reference can act to de-emphasize aspects of the sensor data that would otherwise overwhelm or drown out the aspects that are indicative of a desired biomechanical feature. For example, large amounts of three-dimensional arm swing motion during walking can overwhelm a data processing device attempting to detect a turning event or other biomechanical feature. However, upon translation to the global frame, the resultant movement data may more easily processed and turning events or other biomechanical features more easily detected. In some cases, transforming the sensor data into a global frame can also help with feature engineering in machine learning modeling by reducing the impact of experimental imperfection (e.g. if a wrist-worn sensor were flipped by 90° or 180° degrees across different experiment participants). For example, if a traditional sensor is not oriented properly, the action of walking up stairs, which traditionally exhibits strong signals along the vertical direction, could be easily misclassified as running, which traditionally exhibits strong signals along the anterior direction. Using certain aspects and features of the present disclosure, the movement data resulting from transforming the sensor data from the sensor frame into the global frame would clearly show either vertical or anterior movement, regardless of the orientation and placement of the sensor.

Certain aspects and features of the present disclosure are also especially well-suited to measure and/or detect turn angle, turn velocity, sit-to-stand actions, stand-to-sit actions, falling events, arm swing magnitude, or the like. The aspects and features of the present disclosure can be used to detect other biomechanical features as well.

Certain aspects and features of the present disclosure further relate to automatically identifying the body part at which the sensor is placed. The automatic identification can occur based on sensor data alone or based on a comparison of sensor data to movement data. For example, the individual values within the transformation parameter (e.g., values within the quaternion or rotational matrix) can be analyzed to determine if the sensor whose data is being transform is most likely to be located on the left leg, right leg, left arm, right arm, back, chest, pocket, or any other location. Analyzing the transformation parameter can include comparing the transformation parameter to historical models or comparing values to threshold values. Other techniques can be used to automatically identify the body part at which the sensor is placed. In some cases, systems disclosed herein can receive input from a user or third party interaction to positively identify the body part at which the sensor is placed (e.g., pressing an appropriate button on a wireless-connected computing device).

Once the body part is identified, specific rules associated with movement data from that body part can be used to provide additional insight, detection, or other actions. For example, a sensor used according to certain aspects and features of the present disclosure can provide a signal or alert when a user falls. Fall detection can normally rely primarily on vertical acceleration within the global frame. For example, a sensor placed on a user's chest may experience a large vertical acceleration in the global frame when the user falls. However, if the sensor is placed at a body part already near the floor, such as an ankle-worn sensor, reliance on vertical acceleration may not provide reliable results. Therefore, upon identification that the sensor is placed at an ankle, the system can cause fall detection to rely primarily on in-plane acceleration, rather than vertical acceleration.

Thus, the specific rules associated with identifying particular biomechanical features can be adjusted or selected based on identification of the body part to which the sensor is physically associated (e.g., attached).

Specific details are given in the following description to provide a thorough understanding of certain embodiments. However, certain aspects and features of the present disclosure may be practiced without various specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, or the like. When a process corresponds to a function, its termination can correspond to a return of the function to the calling function or the main function.

The term "machine-readable storage medium" or "computer-readable storage medium" includes, but is not limited to, portable or non-portable storage devices, optical storage devices, and various other mediums capable of storing, containing, or carrying instruction(s) and/or data. A machine-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A machine-readable storage medium may include all or portions of customized hardware, such as application-specific integrated circuits (ASICs). A computer-program product may include code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments may be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a machine-readable medium. A processor(s) may perform the necessary tasks.

Systems depicted in some of the figures may be provided in various configurations. In some embodiments, the systems may be configured as a distributed system where one or more components of the system are distributed across one or more networks in a cloud computing system.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is schematic diagram depicting a system 100 for detecting biomechanical features according to certain aspects of the present disclosure. The system 100 can include at least one sensor 102 worn by a user 110. The user 110 can be an human individual (e.g., a patient), another type of animal, or any suitable movable body (e.g., a robotic device). Sensor 102 is depicted as a wrist-worn sensor, such as a watch or a sensor located within a watch. Other example sensors depicted in FIG. 1 include a chest strap sensor 104, an ankle-worn sensor 106, and a pocketable sensor 108 (e.g., sensor in a phone). Other sensors can be used and can be placed in further locations and/or orientations associated with the user 110. In some cases, a sensor 102 can be removably, permanently, or semi-permanently attached to a user 110. In some cases, a sensor 102 can be directly carried by a user 110 (e.g., in a hand), be located within a user 110 (e.g., an implanted sensor), or be indirectly carried by a user 110 (e.g., supported by an article or object carried by the user, such as a backpack).

The sensor 102 can be any suitable sensor capable of detecting the desired movements. For example, sensor 102 can include at least an accelerometer for detecting acceleration data (e.g., specific force) and a gyroscope for detecting gyroscopic data (e.g., angular velocity). In some cases, a sensor 102 additionally includes a magnetometer for detecting magnetic data (e.g., measurements of the Earth's magnetic field, such as to determine rotational orientation or angular position). In some cases, sensor 102 can be or can include an IMU. Sensor 102 can take measurements and generate sensor data. The sensor data can include any combination of acceleration data, gyroscopic data, and magnetic data. The sensor data represents movement of the sensor 102 within the sensor reference frame 112 (e.g., sensor frame). The sensor reference frame 112 can refer to a coordinate system associated with (e.g., locked to) a particular orientation of the sensor. For example, a sensor may have an arbitrary top side, wherein movement of the sensor in a direction normal to the top side may refer to movement along the Z axis of the sensor's reference frame, regardless of the orientation of the sensor (e.g., whether the top side of the sensor is facing the ground or facing a wall of a room). The orientation of the sensor reference frame 112 is dependent upon the orientation and placement of the sensor 102 on the user 110. Thus, sensor 102 may have a different sensor reference frame 112 than the respective sensor reference frames of chest strap sensor 104, ankle-worn sensor 106, and pocketable sensor 108.

As described in further detail herein, certain techniques can translate sensor data (e.g., acceleration data, gyroscopic data, and/or magnetic data) from the sensor reference frame 112 to a global reference frame 114. The global reference frame 114 can be any standardized or normalized reference. In some cases, the global reference frame 114 is an Earth reference frame associated with a user's 110 orientation on Earth 116. In some cases, the global reference frame 114 is simple a standardized reference frame associated with the user 110 at a starting position (e.g., at rest immediately after turning on the sensor). For example, the global reference frame 114 can be established such that the X direction is collinear or parallel to the user's 110 sagital axis, the Y direction is collinear or parallel to a user's 110 frontal axis, and the Z direction is collinear or parallel to a user's 110 vertical axis. Other orientations can be used for a global reference frame 114. In certain cases, multiple sensors 102 can be used and the respective sensor data from the multiple sensors 102 can be each translated to the same global reference frame 114. Thus, the relative position and orientation between different sensors can be assessed.

The system 100 can operate entirely on a sensor 102 or wearable device comprising the sensor 102. For example, a wearable device can include sensor 102, as well as sufficient components (e.g., power, processor, memory, and the like) to perform the operations described herein. For example, the wearable device may be able to obtain the sensor data, detect reference events, calculate transformation parameters, transform the sensor data into movement data in the global reference frame 114, and even determine biomechanical features and possibly generate diagnosis inferences. In some cases, certain processing tasks can be relayed to additional devices. For example, in some cases system 100 can include a server 120. Server 120 can communicate with sensor 102 through a wired or wireless network, such as through the Internet (e.g., through a cloud). Transmissions 120 between the sensor 102 and the server 120 can include sensor data (e.g., in the sensor reference frame 112), transformation parameters, movement data (e.g., in the global reference frame 112), determined biomechanical features, and/or generated diagnostic inferences.

For example, in some cases, the wearable device collects sensor data using the sensor 102 and transmits the sensor data to the server 120 for processing. The server 120 can detect reference events, calculate transformation parameters, and send back those transformation parameters. Thus, certain computationally expensive processing can be offloaded to the server 120, while still allowing the wearable device to transform sensor data into movement data on the fly. The server 120 can also transform the received sensor data into movement data and send back the movement data to the wearable device, thus allowing additional computationally expensive processing to be offloaded to the server 120. The server 120 can also perform any additional processing as described herein and send back to the wearable device any data as necessary. In some cases, the server 120 sends no data back to the wearable device, and instead stores the data (e.g., sensor data, movement data, and/or any other inferred or determined data or results) for later access or transmits data to an additional device, such as a user's phone 118 or a healthcare provider's computer.

In some cases, an additional device, such as a user's phone 118, can handle the same offloading functions described above with reference to the server 120. In some cases, an additional device, such as a user's phone 118, can act as a relay between the wearable device and the server 120, with transmissions 122, 124 occurring between the wearable device and the phone 118 and the phone 118 and the server 120, respectively. In some cases, the phone 118 can perform some or all of the processing and data storage/serving processes described above with reference to the server 120. For example, the system 100 can be set up so that detection of reference events and calculation of transformation parameters is performed by the server 120, which sends the current transformation parameter or updates thereto to the phone 118, which receives sensor data from the sensor 102 of the wearable device and performs transformations on the sensor data using the transformation parameters received by the server 120. Thus, realtime of offline movement data can be generated on the phone 118 using the currently stored transformation parameters. When necessary, occasionally, or continuously, the phone 118 can relay sensor data to the server 120 and can receive, in response, an updated transformation parameter. Other offloading and/or co-processing schemes can be used with any combination of computing devices.

Figure 2:
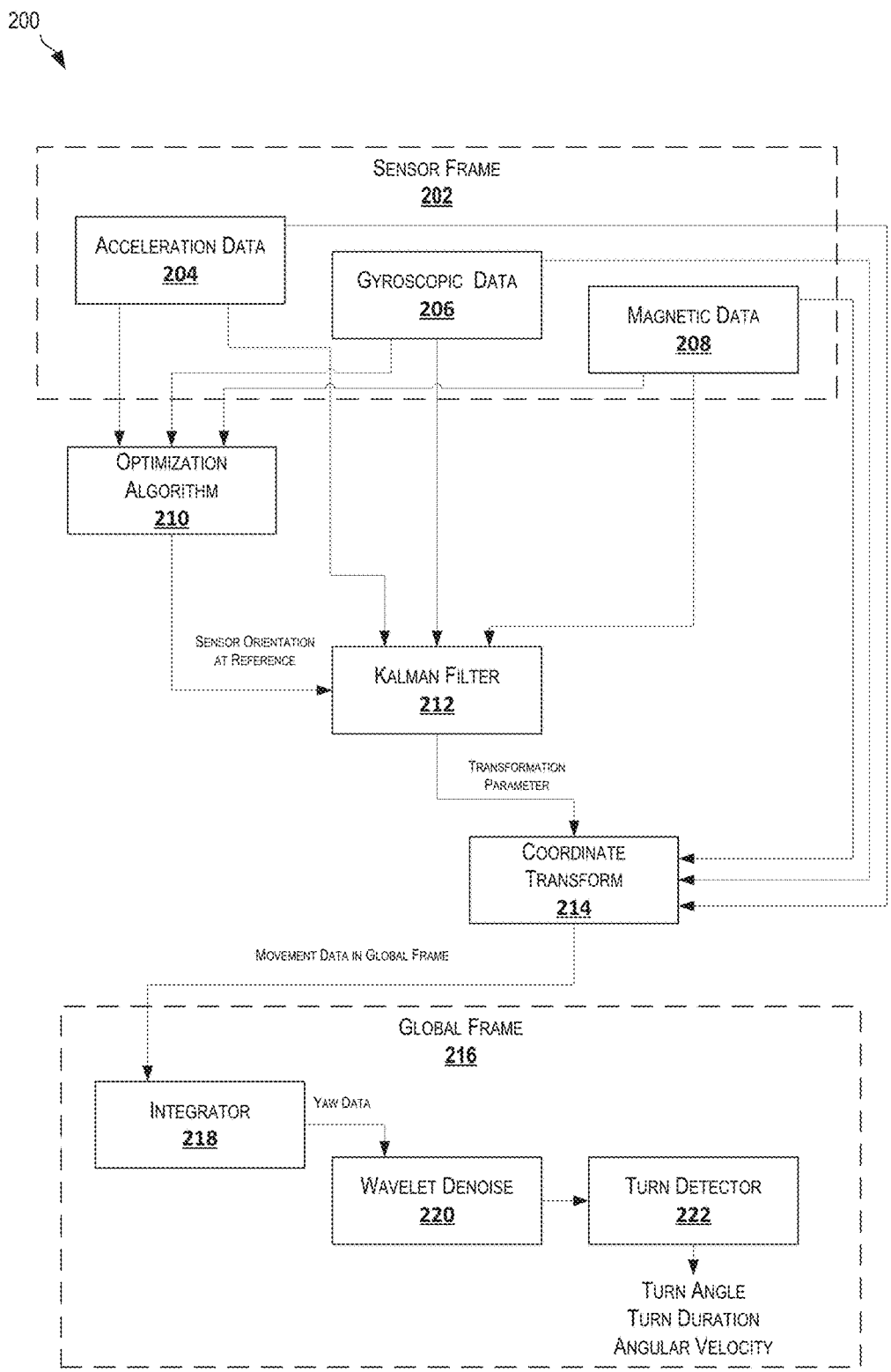
FIG. 2 is a schematic flowchart depicting a process for converting sensor frame data to global frame data according to certain aspects of the present disclosure.

FIG. 2 is a schematic flowchart depicting a process 200 for converting sensor frame data to global frame data according to certain aspects of the present disclosure. At block 204, acceleration data in the sensor frame 202 (e.g., sensor reference frame) can be obtained. At block 206, gyroscopic data in the sensor frame 202 can be obtained. At block 208, magnetic data in the sensor frame 202 can be obtained.

At block 210, the acceleration data 204, the gyroscopic data 206, and the magnetic data 208 can be processed using an optimization algorithm. In some cases, if one or more of the acceleration data 204, the gyroscopic data 206, or the magnetic data 208 is unavailable, the remaining data will be used at block 210. The result of the optimization algorithm can be a determination of the sensor's orientation (e.g., attitude) at a particular time. The optimization algorithm at block 210 can be performed when the sensor is known or otherwise determined to be at a reference position, thereby outputting data associated with the sensor's orientation at the time of a reference event, also known as a reference orientation. In some cases, additional data other than acceleration data 204, gyroscopic data 206, or magnetic data 208 can be used in the optimization algorithm, such as image data associated with known locations/positions.

The orientation data from block 210 can be provided to a filter at block 212, along with acceleration data 204, gyroscopic data 206, and magnetic data 208. At block 210, the filter can use the its received data to generate a transformation parameter. The filter at block 212 can be a Kalman filter, such as an Extended Kalman filter. In some cases, other filters, such as a complementary filter, can be used to generate the transformation parameter. The transformation parameter generated at block 212 can be a quaternion or other suitable parameter usable to transform movement data from the sensor frame 202 to movement data in the global frame 216. For example, the transformation parameter can be a rotational matrix. In some cases, a first transformation parameter can be converted to a different transformation parameter to facilitate downstream computations.

At block 214, the transformation parameter from block 212 is applied to movement data from the sensor frame 202, such as acceleration data 204, gyroscopic data 206, and/or magnetic data 208. Applying the transformation parameter to the movement data from the sensor frame 202 can transform the coordinate from the sensor frame 202 to the global frame 216, resulting in movement data in the global frame 216.

In some cases, process 200 can optionally include additional steps associated with the movement data in the global frame. As depicted in FIG. 2, process 200 includes additional blocks for detecting biomechanical features related to turning events (e.g., a user walking and turning). For example, at block 218, rotational acceleration data in the global frame can be integrated using an integrator 218 to generate yaw data (e.g., yaw data in the global frame, such as rotation about a user's vertical axis). At block 220, the yaw data can be optionally denoised using a wavelet denoise process (e.g., a discrete wavelet transformation and kernel smoother). The resulting denoised yaw data can be provided to a turn detector at block 222. The turn detector can analyze the denoised yaw data and calculate, measure, or otherwise detect various biomechanical features associated with the yaw data. For example, the turn detector can use the denoised yaw data to generate turn angle measurements, turn durations, and angular velocity during turns.

Figure 3:
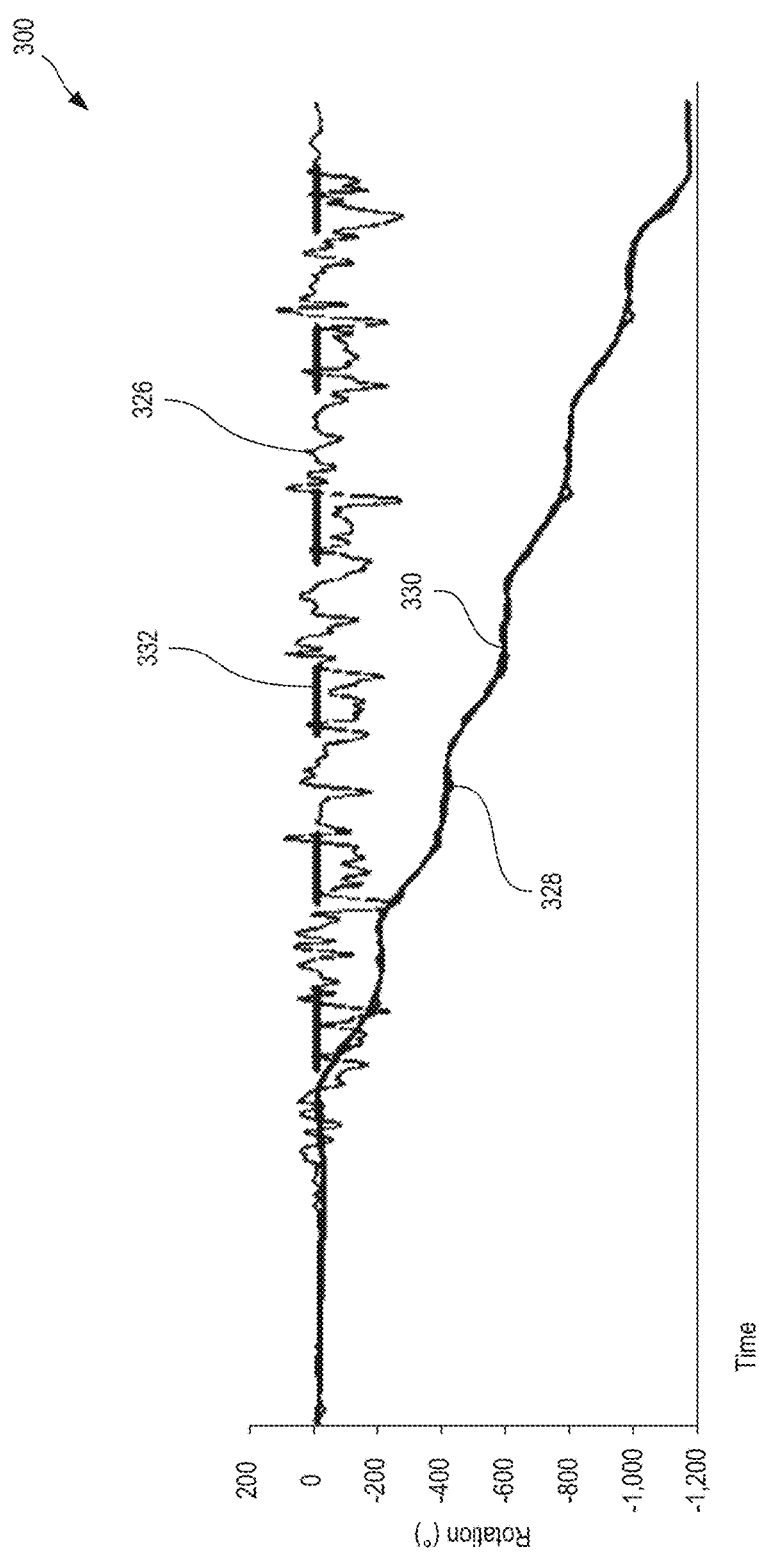
FIG. 3 is a chart depicting turn detection data over time from a wrist-worn sensor according to certain aspects of the present disclosure.

FIG. 3 is a chart 300 depicting turn detection data over time from a wrist-worn sensor according to certain aspects of the present disclosure. The chart 300 in FIG. 3 depicts gyroscopic data 326 (Earth frame of reference), cumulative turn angle data 328, denoised cumulative turn angle data 330, and detected turn events 332. The gyroscopic data 326 can be gyroscopic data in the global frame 216 from block 214 of FIG. 2. The cumulative turn angle data 328 can integrated yaw data from block 218 of FIG. 2. The denoised cumulative turn angle data 330 can be the denoised yaw data from block 220 of FIG. 2. The detected turn events 332 can be turn durations detected by the turn detector at block 222 of FIG. 2.

As evident from chart 300, the gyroscopic data 326 in the Earth frame can be used to accurately and reliably detect turn events 332. Therefore, regardless of the position or orientation of the sensor being used to obtain the gyroscopic data 326 in the Earth frame, the transformation of the sensor frame data to the Earth frame allows for a data processor to perform a standard set of processes (e.g., blocks 218, 220, 222 of FIG. 2) to generate a desired output (e.g., detection of biomechanical features).

Figure 4:
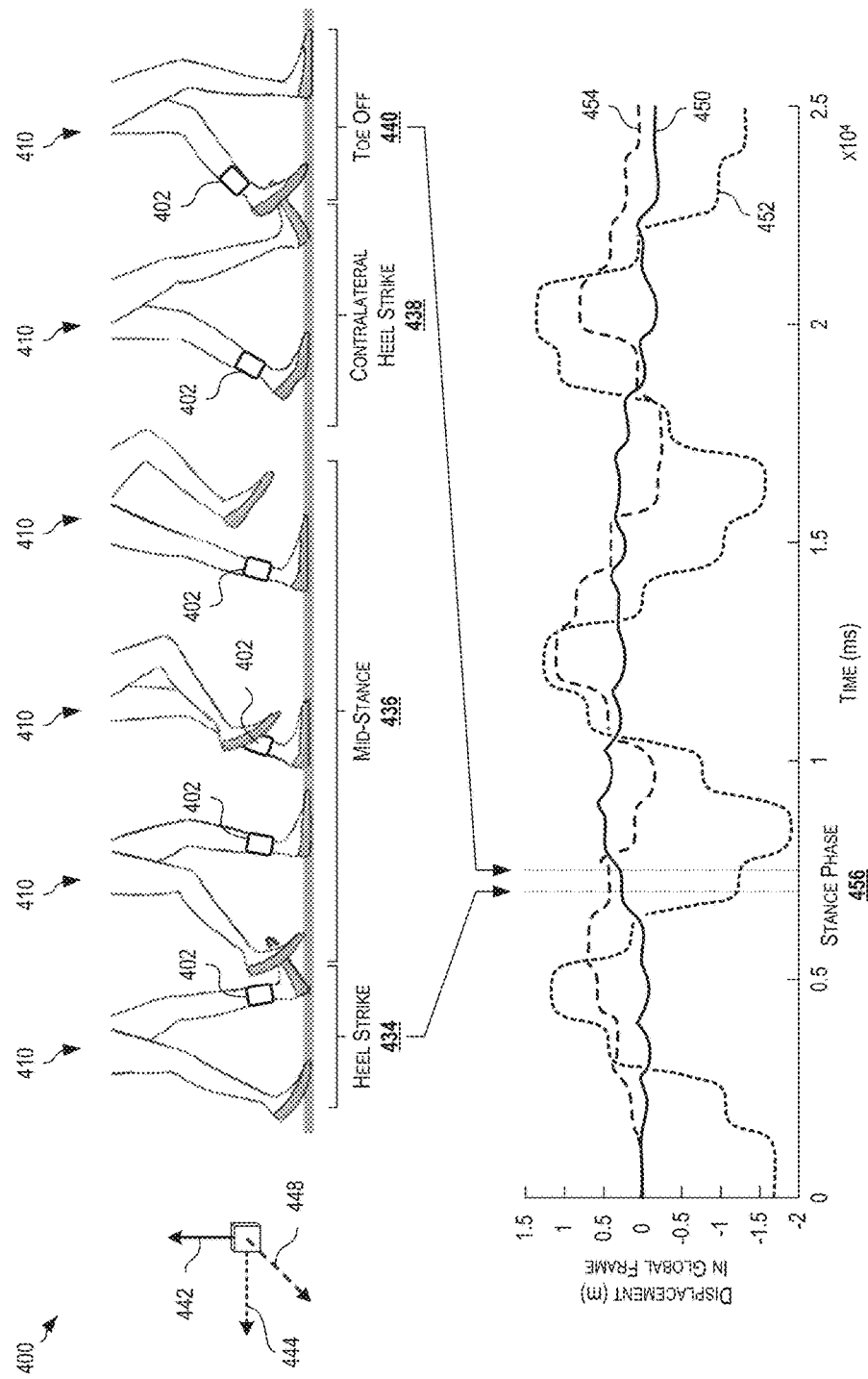
FIG. 4 is a chart depicting movement in the global frame of an ankle-worn device during walking actions according to certain aspects of the present disclosure.

FIG. 4 is a chart 400 depicting movement in the global frame of an ankle-worn device 402 during walking actions according to certain aspects of the present disclosure. An ankle-worn device 402 is depicted on the left leg of an individual 410, although it can be placed elsewhere. The chart 400 plots displacement in meters of the ankle-worn device 402 over time for the individual 410 walking during three repetitive forward/backward paths. A portion of the walking time is called out in a schematic time-lapse diagram of the individual 410 at different times. The individual 410 can move between a heel strike 434 and a toe off 440 and then on to another heel strike. At the heel strike 434, the heel of the left foot (e.g., the foot associated with the leg to which the sensor is attached) strikes the floor. At mid-stance 436, the individual 410 can move through several mid-stance positions (e.g., early, middle, and late mid-stance positions), during which individual's 410 left foot is planted on the floor while the right leg swings. At contralateral heel strike 438, the heel of the right foot (e.g., the foot associated with the leg to which the sensor is not attached) strikes the floor. At toe off 440, the toe of the left foot lifts from the floor. The time between the heel strike 434 and the toe off 440 can be referred to as the stance phase 456.

During the stance phase 456, it may be safe to make certain assumptions about the position and/or orientation of the ankle-worn device 402. These assumptions can include assuming that the sensor of the ankle-worn device 402 is in a particular reference orientation.

The sensor of the ankle-worn device 402 can operate in a sensor frame of reference, having its own X, Y, and Z axes. As described herein, the sensor data can be converted to a global frame, the global frame having an X axis 442, a Y axis 444, and a Z axis 448. As used with respect to FIG. 4, the X axis 442 represents a vertical (e.g., up/down) direction with respect to the individual 410 as depicted in FIG. 4, the Y axis 444 represents a forward/backward direction with respect to the individual 410, and the Z axis 448 represents a left/right direction with respect to the individual 410. The sensor data generated by the ankle-worn device 402, after being converted to the global frame, can be used to plot displacement in meters along the X axis 442, Y axis 444, and Z axis 448. For example, accelerometer data can be integrated to determine velocity data, which can be integrated to determine position data. In chart 400, line 450 depicts X axis 442 displacement (e.g., vertical displacement) over time, line 452 depicts Y axis 444 displacement (e.g., forwards/backwards displacement) over time, and line 454 depicts Z axis 442 displacement (e.g., left/right displacement) over time.

From the data depicted in chart 400, it is possible to identify when an individual 410 is in a stance phase 456. For example, when lines 450, 452, 454 are all flat or nearly flat, it can be assumed that the sensor is at rest. Certain patterns in one or more of lines 450, 452, 454 can be correlated with heel strike 434, mid-stance 436, contralateral heel strike 438, and toe off 440. Thus, it can be possible to identify when the individual 410 is in a stance phase 456. In some cases, an individual 410 entering a stance phase 456 can be a type of reference event which can trigger processes used to determine translation parameters, as described herein.

In some cases, entering a stance phase 456, or another reference event, can be determined using raw sensor data that has not been converted to the global frame. Expected patterns in raw sensor data can be indicative of certain reference events. In some cases, determination of a reference event, such as a stance phase 456, using sensor data in the sensor frame can provide feedback to the transformed measurement data in the global frame. For example, when a stance phase 456 is detected, it can be assumed that the velocity of the foot in the global frame is at or near zero. Therefore, if, after transforming the sensor data to measurement data in the global frame, the measurement data associated with velocity of the foot is not at or near zero, a correction can be applied to adjust the measurement data such that the velocity of the foot reads at or near zero. In this fashion, occasional drift and deviations can be corrected automatically and dynamically, leading to more accurate and reliable measurement data.

Figure 5:
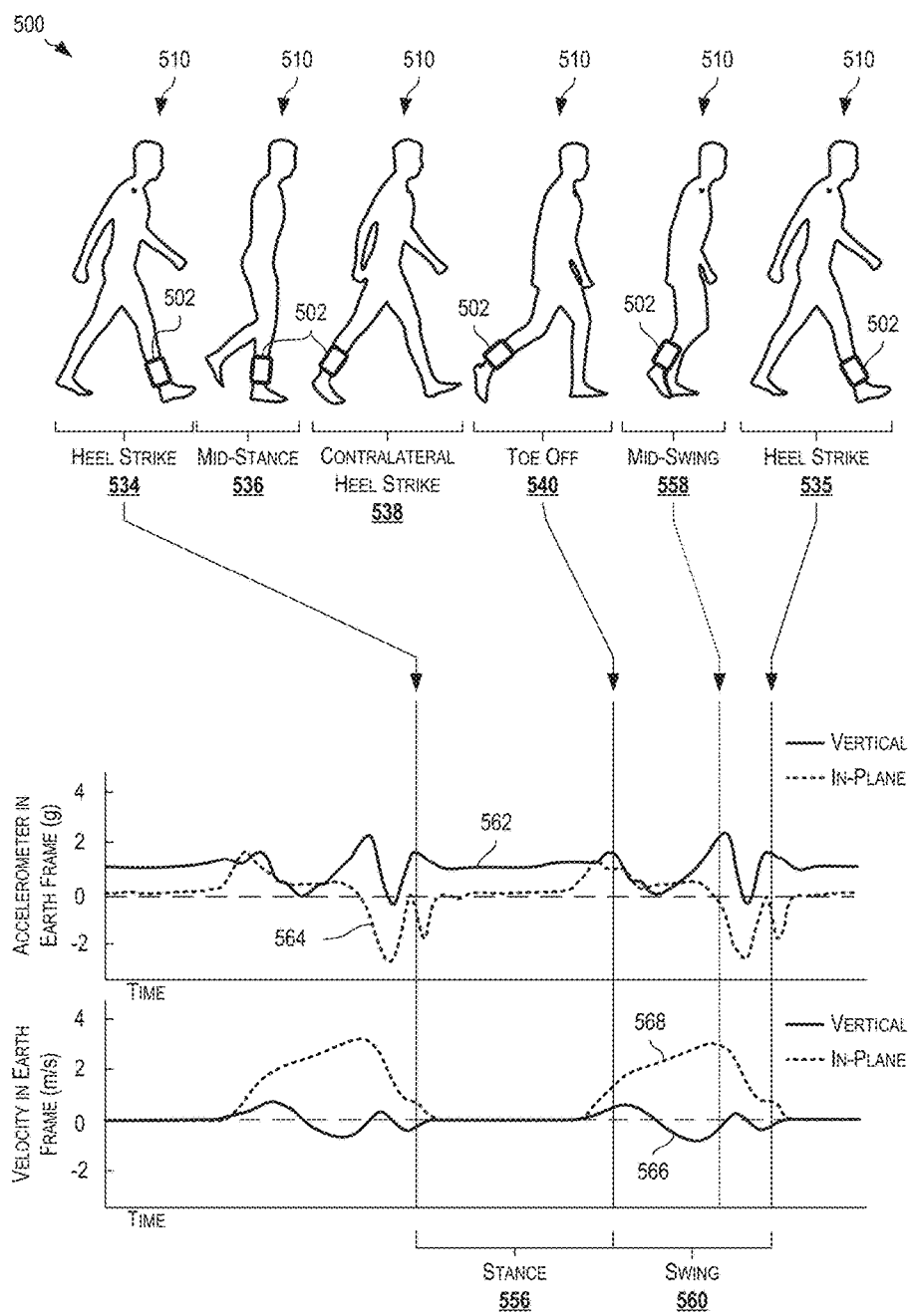
FIG. 5 is a chart depicting movement in the Earth frame of an ankle-worn device during walking actions according to certain aspects of the present disclosure.

FIG. 5 is a chart 500 depicting movement in the Earth frame of an ankle-worn device 502 during walking actions according to certain aspects of the present disclosure. The ankle-work device 502 can be similar to ankle-worn device 402 of FIG. 4. The data associated with chart 400 of FIG. 4 can be used to generate the data associated with chart 500.

An ankle-worn device 502 is depicted on the right leg of an individual 510, although it can be placed elsewhere. The chart 500 plots acceleration and velocity in the Earth frame, although any other global frame can be used. Acceleration is plotted in units of standard gravity (G), such that a value of 1.0 is equal to at or approximately 9.8 m/s$^2$. Velocity is plotted in units of meters per second. The time axes are left dimensionless, as they depend on walking speed of the individual 510.

A portion of the walking time is called out in a schematic time-lapse diagram of the individual 510 at different times. The individual 510 can move between heel strike 534 and a toe off 540 and then on to another heel strike 535. At the heel strike 534, the heel of the right foot (e.g., the foot associated with the leg to which the sensor is attached) strikes the floor. At mid-stance 536, the individual's 510 right foot is planted on the floor while the left leg swings. At contralateral heel strike 538, the heel of the left foot (e.g., the foot associated with the leg to which the sensor is not attached) strikes the floor. At toe off 540, the toe of the right foot lifts from the floor. At mid-swing 558, the right leg is swinging while the left foot remains planted. The right leg is generally moving at a maximum speed during mid-swing 558. At heel strike 535, the heel of the right foot returns to the floor. The time between the heel strike 534 and the toe off 540 can be referred to as the stance phase 556. The time between toe off 540 and heel strike 535 can be referred to as the swing phase 560.

During the stance phase 556, it may be safe to make certain assumptions about the position and/or orientation of the ankle-worn device 502. These assumptions can include assuming that the sensor of the ankle-worn device 502 is in a particular reference orientation.

In chart 500, line 562 depicts vertical acceleration over time, line 564 depicts in-plane (e.g., parallel to the ground) acceleration over time, line 566 depicts vertical velocity over time, and 568 depicts in-plane velocity over time.

From the data depicted in chart 500, it is possible to identify when an individual 510 is in a stance phase 556 or a swing phase 560. Certain patterns in one or more of lines 562, 564, 566, 568 can be correlated with heel strike 534, mid-stance 536, contralateral heel strike 538, toe off 540, mid-swing 558, and heel strike 535. For example, heel strike 534 or heel strike 535 can be correlated with a local maximum in line 562 immediately following a local-maximum in line 564, as is associated with the shock when the heel strikes the ground immediately following the forward movement of the foot rapidly slowing when the heel hits the ground. A stance phase 556 can be correlated with a relatively constant line 562 at or near 1.0 and a relatively constant line 556. Toe-off 540 can be correlated with a decrease in line 562 and a local maximum in line 564, as expected due to the sudden forward and upward movement of the foot during toe-off 540. During mid-swing, a local maximum in line 568 can be expected, as the leg is swinging at its fastest speed.

Figure 6:
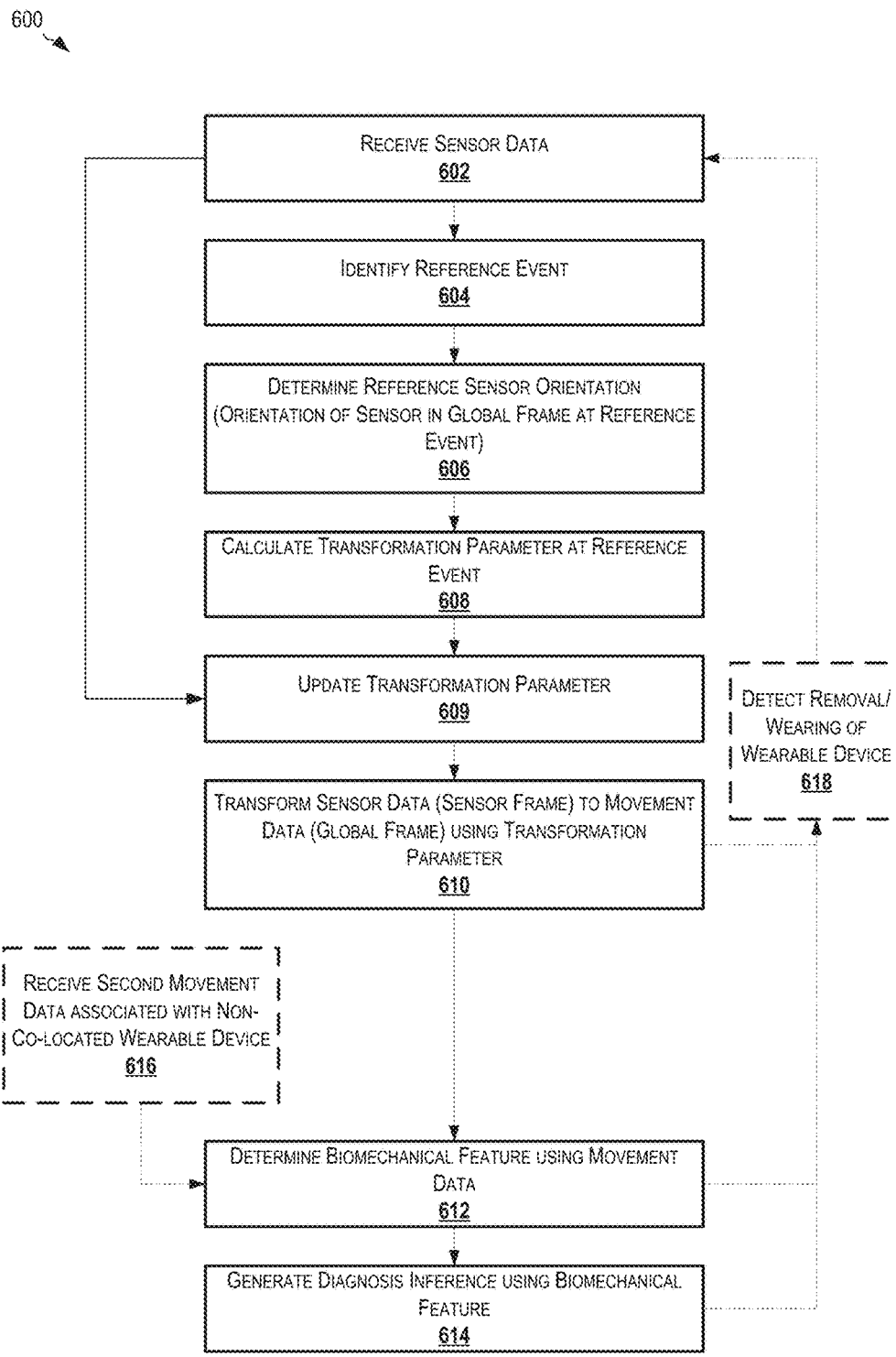
FIG. 6 is a flowchart depicting a sensor-location-agnostic process for determining biomechanical features according to certain aspects of the present disclosure.

FIG. 6 is a flowchart depicting a sensor-location-agnostic process 600 for determining biomechanical features according to certain aspects of the present disclosure. Any suitable device can perform some or all of process 600, such as a wearable device, a server, or any other computing device (e.g., a smartphone). While depicted as sequential blocks for illustrative purposes, various aspects of process 600 can be performed sequentially and/or simultaneously.

At block 602, sensor data can be received. In some cases, sensor data can be received at a wearable device, directly from a sensor. In some cases, a separate device (e.g., server) can receive sensor data via a transmission (e.g., wired or wireless) from a sensor or a wearable device. Receiving sensor data can include receiving any combination of acceleration data, gyroscopic data, and magnetic data. The sensor data is in the sensor frame of reference. Receiving sensor data at block 602 can include receiving a finite amount of data (e.g., a finite number of data points) or continuously receiving sensor data. The sensor data can be associated with (e.g., indicative of) movement of a wearable device in the sensor frame.

At block 604, a reference event can be identified. Identifying a reference can include receiving a communication indicative that a reference event has occurred (e.g., a signal originating from a user depressing a calibration button). In some cases, identifying a reference event can occur automatically or dynamically, such as through analysis of the sensor data received at block 602. As described with reference to the example of FIG. 4, it can be possible to determine the occurrence of a reference event through analysis of sensor data. Any suitable analysis can be conducted on the sensor data, including looking for patterns, trends, threshold values, or the like. In some cases, identifying a reference event at block 604 can include comparing the sensor data to models generated through machine learning and/or historical models.

In some cases, additional data can be used to identify a reference event. For example, heart rate variability can be monitored through a heart rate sensor. When certain patterns in the heart rate variability are sensed, it can be inferred that a reference event has occurred.

At block 606, the reference sensor orientation can be determined. The reference sensor orientation can include at least some position and/or orientation information related to the sensor in the global frame. For example, if the reference event identified at block 604 is a stance phase of a walking gait, the reference sensor orientation may include information about the acceleration, velocity, and/or rotational speed of the sensor in the global frame, such as an assumption that at the stance phase, the sensor should have at or near zero velocity, at or near zero yaw rotational speed, flat acceleration (e.g., at 1 g).

At block 608, the sensor data from block 602 and the reference sensor orientation from block 606 can be used to determine a transformation parameter associated with the reference event. In some cases, calculating a transformation parameter can include supplying at least some data from the sensor data and the reference sensor orientation information to an extended Kalman filter. Determining a transformation parameter can be a computationally expensive process. In some cases, it can be desirable to offload the processing of the transformation parameter to an additional device, such as a smartphone or a server (e.g., a cloud of servers). The transformation parameter can be a quaternion or a rotational matrix, although other parameters may be used.

At block 609, the transformation parameter can be updated. In some cases, updating the transformation parameter can occur in real-time and/or can use real-time sensor data. The transformation parameter can be updated by determining a change in position of the sensor since a previous (e.g., immediately previous) position for which a transformation parameter has been calculated or updated.

This change can then be used to apply necessary updates to the transformation parameter such that the updated transformation parameter is usable to transform the current sensor data into movement data in the global frame. In some cases, the transformation parameter can be updated iteratively, with incremental changes being applied to previously updated transformation parameters. In some cases, updated transformation parameters can be individually calculated based on the originally calculated transformation parameter at the reference event from block 608 and a calculation of changes in the sensor's position since the reference event. When updated iteratively, the transformation parameter can be updated on a frame-by-frame basis as new sensor data is obtained. In some cases, the transformation parameter is updated based on a certain preset amount of recent data (e.g., past 30 frames, past 5 seconds, or the like).

At block 610, the transformation parameter can be applied to sensor data in the sensor frame to calculate movement data in the global frame. In some cases, only particular data types of the sensor data are transformed, such as only acceleration data or only acceleration and gyroscopic data. In some cases, all data types of the sensor data are transformed. In some cases, only particular a particular set of datapoints of the sensor data are transformed. In other cases, all of the sensor data is transformed. In some cases, sensor data is transformed dynamically as it is collected. For example, a wearable device can store a transformation parameter (e.g., obtained from a server or calculated within the wearable device itself) in local memory and can use it to dynamically convert incoming sensor data into movement data in the global frame as the sensor data is being collected. As described in further detail herein, the transformation parameter can be updated, in which case the wearable device can store and use the updated transformation parameter to provide dynamic movement data based on continuously collected sensor data.

At optional block 612, a biomechanical feature can be detected. In some cases, the biomechanical feature can be a sensor-location-agnostic biomechanical feature (e.g., a feature that is not related to sensor position), such as turn rate while walking. In some cases, a sensor-location-specific biomechanical feature can be determined, such as leg speed during swing phases. The biomechanical feature can be determined using movement data calculated at block 610. In some cases, sensor data can also be used, along with movement data, to determine certain biomechanical features.

In some cases, at optional block 616, second movement data associated with another wearable device can be received. The second movement data can be calculated in a fashion similar to blocks 602, 604, 606, 608, 610 of process 600. The second movement data can be associated with a wearable device that is not collocated with the wearable device providing sensor data at block 602. As used herein with reference to sensors and/or wearable devices, the term "non-co-located" can include one object having a different position and/or orientation than, being located at a distance from, or being located on or supported by a different body part than the other object, while nevertheless being associated with movement of the user. In some cases, determining a biomechanical feature at block 612 can additional include using the second movement data received at block 616. In some cases, more than two sets of movement data, associated with more than two non-co-located wearable devices, can be used to determine biomechanical features.

At optional block 614, a diagnosis inference can be generated using the biomechanical feature determined at block 612. The diagnosis inference can be generated by comparing the biomechanical feature with threshold values, models, or otherwise analyzing the biomechanical feature to determine if the values and/or patterns of the biomechanical feature are correlated with a diagnosis inference. A diagnosis inference can include likelihood of increased or decreased risk of a condition or disease, likelihood of severity of a condition or disease, or any other conclusions correlated with the biomechanical feature from block 612. In some cases, a diagnosis inference is generated using the biomechanical feature and other diagnostic data, such as pulse rate variability.

In some cases, at optional block 618, a detection can be made that the wearable device has been removed and/or re-worn. The detection can be as simple as receiving outlier sensor data for a threshold period, receiving no sensor data for a period, receiving a power-off indication, receiving a removal indication, or any other such indication that the wearable device has been removed. In some cases, no actual detection is made, however the device can be removed and replaced at a later time. Replacing or re-wearing the wearable device need not be in the same location as from where the wearable device was removed. In some cases, the location of the wearable device after re-wearing is not known to the system. After this detection, the process 600 can continue from block 602 and a new transformation parameter specifically associated with the currently unknown location of the wearable device can be calculated at block 608. Block 618 can occur at any point in time, but in some cases will occur after any of blocks 610, 612, 614.

Figure 7:
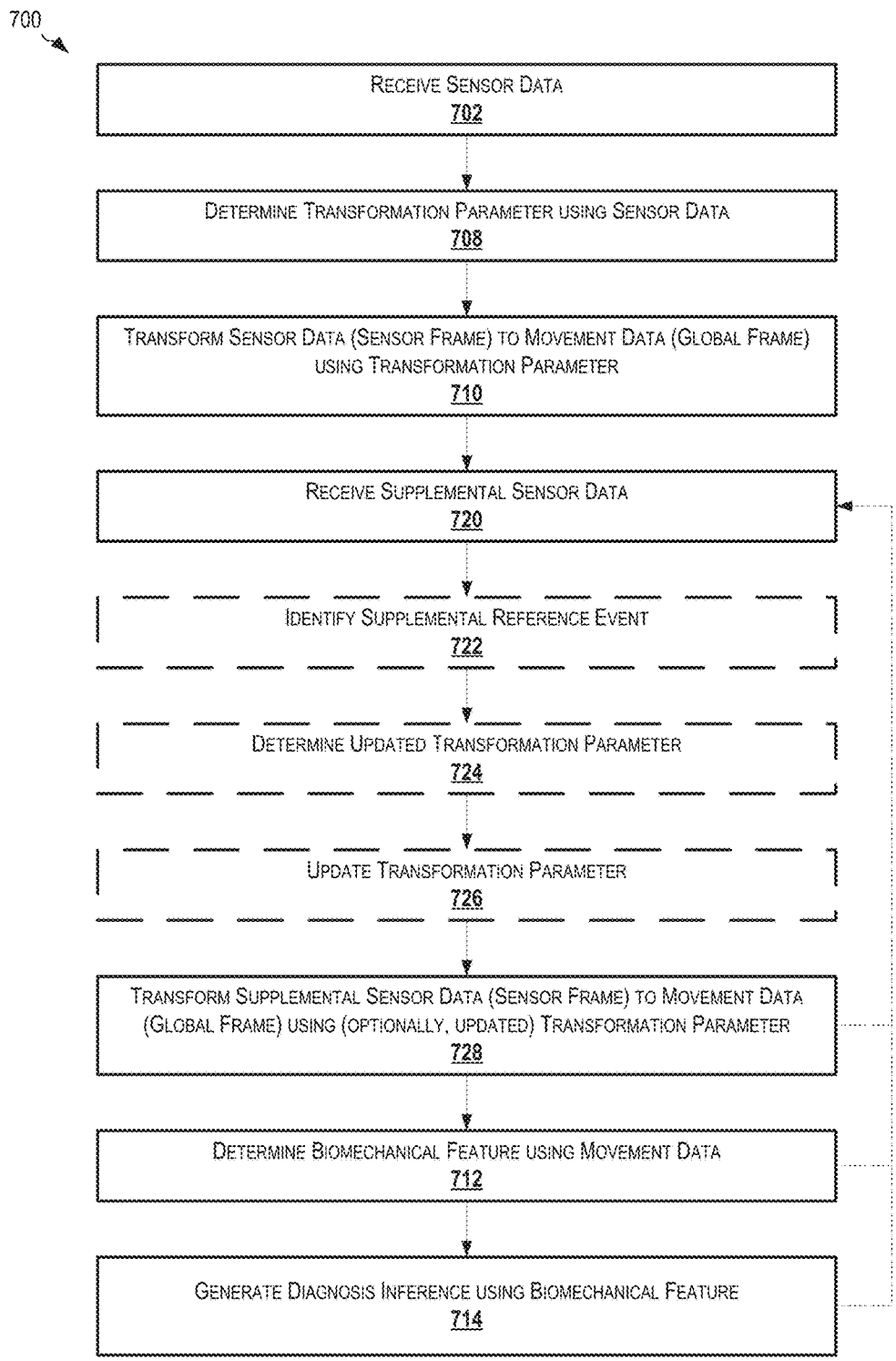
FIG. 7 is a flowchart depicting a dynamically updating, sensor-location-agnostic process for determining biomechanical features according to certain aspects of the present disclosure.

FIG. 7 is a flowchart depicting a dynamically updating, sensor-location-agnostic process 700 for determining biomechanical features according to certain aspects of the present disclosure. Any suitable device can perform some or all of process 700, such as a wearable device, a server, or any other computing device (e.g., a smartphone). While depicted as sequential blocks for illustrative purposes, various aspects of process 700 can be performed sequentially and/or simultaneously.

At block 702, sensor data is received similar to receiving sensor data at block 602 of FIG. 6. At block 708, a transformation parameter can be determined using the sensor data from block 702. The transformation parameter can be determined (e.g., calculated) as described with reference to process 600 of FIG. 6. At block 710, the sensor data of block 702 can be transformed, using the transformation parameter of block 708, into movement data in a global frame.

At block 720, supplemental sensor data can be received. Supplemental sensor data can be received similarly to receiving sensor data at block 702, however after a transformation parameter has already been determined at block 708.

At optional block 722, a supplemental reference event can be identified using the supplemental sensor data. The supplemental reference event can be identified similarly to identifying the reference event at block 604 of FIG. 6. At optional block 724, an updated transformation parameter can be determined using the supplemental reference event (e.g., using a supplemental reference orientation associated with the supplemental reference event). The updated transformation parameter can be determined similarly to determining the transformation parameter at block 708, however based on the supplemental sensor data of block 720. At optional block 726, the transformation parameter from block 708 can be updated using the updated transformation parameter of block 724.

At block 728, the supplemental sensor data can be transformed into movement data in the global frame. The transformation at block 728 can include applying a transformation parameter to the supplemental sensor data of block 720. The transformation parameter can be the transformation parameter of block 708, an updated transformation parameter of block 724, or the transformation parameter of block 708 after it has been updated using the transformation parameter of block 724.

At optional block 712, a biomechanical feature can be detected. In some cases, the biomechanical feature can be a sensor-location-agnostic biomechanical feature (e.g., a feature that is not related to sensor position), such as turn rate while walking. In some cases, a sensor-location-specific biomechanical feature can be determined, such as leg speed during swing phases. The biomechanical feature can be determined using movement data calculated at block 710. In some cases, sensor data or supplemental sensor data can also be used, along with movement data, to determine certain biomechanical features.

At optional block 714, a diagnosis inference can be generated using the biomechanical feature determined at block 712. The diagnosis inference can be generated by comparing the biomechanical feature with threshold values, models, or otherwise analyzing the biomechanical feature to determine if the values and/or patterns of the biomechanical feature are correlated with a diagnosis inference. A diagnosis inference can include likelihood of increased or decreased risk of a condition or disease, likelihood of severity of a condition or disease, or any other conclusions correlated with the biomechanical feature from block 712.

In some cases, the process 700 can repeat by proceeding to block 720 after any one of blocks 728, 712, 714. In some cases, supplemental sensor data 720 can occur continuously.

Figure 8:
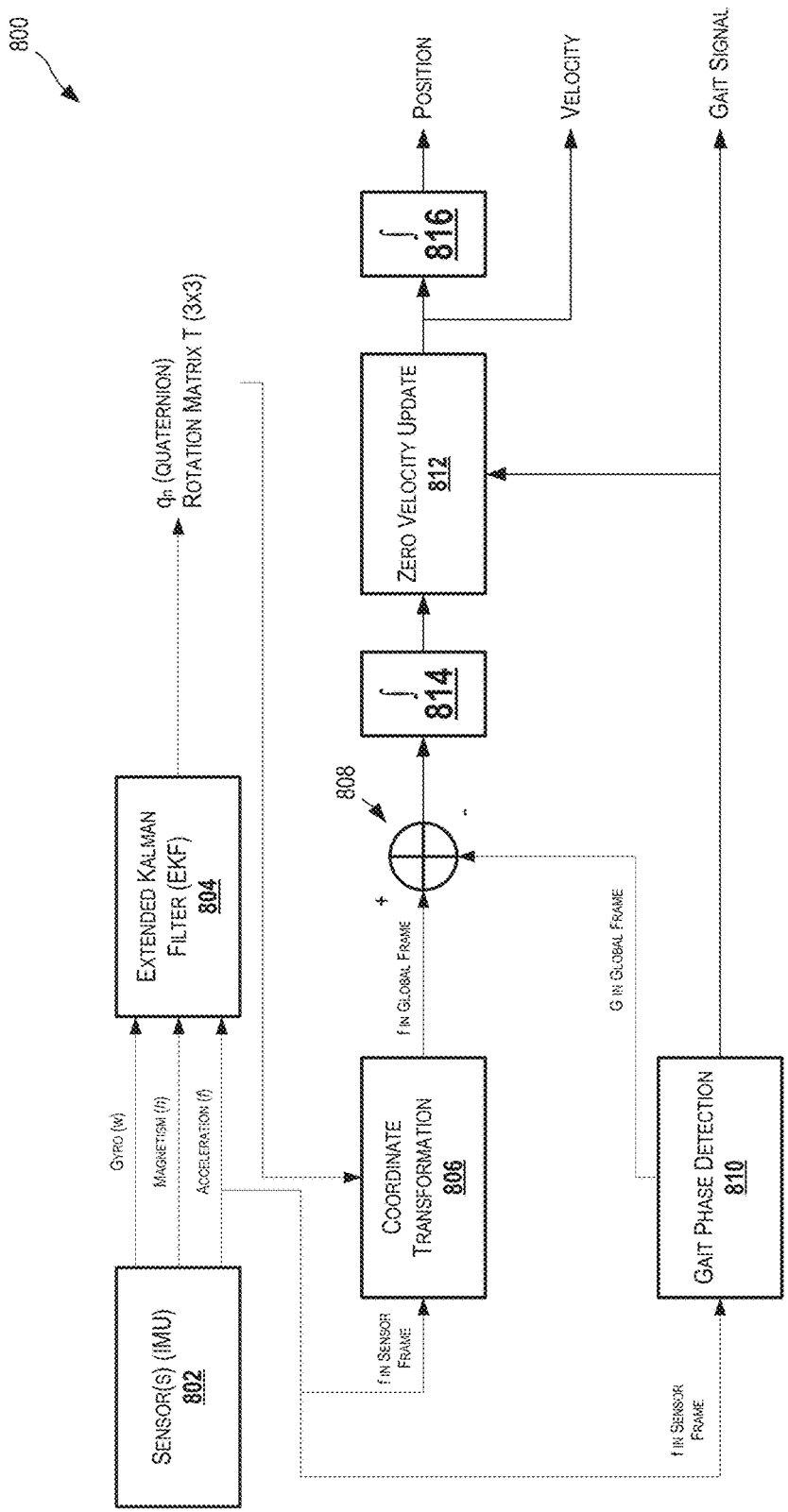
FIG. 8 is a schematic diagram depicting a system for transforming sensor frame data to global frame data and correcting deviations according to certain aspects of the present disclosure.

FIG. 8 is a schematic diagram depicting a system 800 for transforming sensor frame data to global frame data and correcting deviations according to certain aspects of the present disclosure. Sensor(s) 802 can generate gyroscopic data, magnetism data, and/or acceleration data. Sensor 802 can be an IMU. Some or all of the gyroscopic data, magnetism data, and/or acceleration data can be passed to an extended Kalman filter (EKF) 804. The EKF 804 can process the sensor data to generate an estimation of the orientation of the sensor 802 in a global frame. As a result, the transformation information necessary to convert the sensor data in the sensor frame to the estimated orientation in the global frame can determined and a transformation parameter, such as quaternion or rotational matrix, can be calculated.

In the example depicted in FIG. 8, acceleration is used for further processing, however further processing can use any combination of gyroscopic data, magnetism data, and/or acceleration data. Acceleration data in the sensor frame can be provided to a coordinate transformation module 806, along with the transformation parameter (e.g., quaternion or a rotational matrix).

In one example, acceleration in the global frame ($f_{global}$) can be calculated by the coordinate transformation module 806 using acceleration in the sensor frame ($f_{sensor}$) and a quaternion according to the equation $f_{global} = q_n \otimes f_{sensor} \otimes \text{conj}(q_n)$, where $q_n$ is the quaternion and $\text{conj}(q_n) = q^* = -\frac{1}{2}(q + iqi + jqj + kqk)$.

In another example, acceleration in the global frame ($f_{global}$) can be calculated by the coordinate transformation module 806 using acceleration in the sensor frame ($f_{sensor}$) and a rotational matrix according to the equation $f_{global} = T^* f_{sensor}$, where T is a rotational matrix. In some cases, rotational matrix (T) can be a 3×3 matrix.

The output of the coordinate transformation module 806 can be movement data in the global frame. For dynamic correction, sensor data in the sensor frame can be compared with movement data in the global frame at certain times (e.g., upon occurrence of a reference event). The example depicted in FIG. 8 is a walking gait correction example with a ankle-worn sensor, such as those described with reference to FIGS. 4 and 5. However, other examples can be used.

Acceleration data in the sensor frame can be provided to a gait phase detection module 810. The gait phase detection module 810 can detect and identify reference events, such as instances when the user is in a stance phase. At a stance phase, the sensor is expected to have constant acceleration force due to gravity and to have a zero velocity due to the foot being planted on the ground.

Upon detection of the reference event, the acceleration in the global frame ($f_{global}$) can be offset at block 808 by the known or expected constant acceleration force due to gravity. Since the system is sensor-location-agnostic, known or expected constant offsets, such as due to gravity, cannot be accounted for until after the sensor data has been transformed into the global frame, where the direction of gravity is known with respect to the global frame. This corrected acceleration data in the global frame can be provided to an integrator 814 to generate velocity data in the global frame.

In some cases, the velocity data in the global frame can be supplied to a zero velocity update module 812 to apply a correction to the velocity data in the global frame. Since the gait phase detection module 810 can detect reference events, the gait phase detection module 810 can supply the zero velocity update module 812 with an indication of when the velocity in the global frame is expected to be zero (e.g., occurrence of a zero-expected-velocity event), such as during a stance phase. Upon receiving this indication, the zero velocity update module 812 can adjust the velocity data in the global frame received from integrator 814 by whatever amount is necessary to achieve a zero velocity. The zero velocity update module 812 can calculate an offset between the velocity data from integrator 814 and zero at the time of the zero-expected-velocity event, then correct the velocity data by applying that offset to the velocity data from the integrator 814. This action can occur for velocities in any suitable directions. In some cases, other zero-expected-velocity events can be detected other than phases of a gait. In some cases, the zero velocity update module 812 can retain the adjustment amount (e.g., offset) to correct incoming velocity data after the zero-expected-velocity event (e.g., between zero-expected-velocity events). The corrected velocity data in the global frame can be output as velocity data and/or supplied to an integrator 816 for calculation of position data (e.g., relative position data) in the global frame.

In some cases, the gait phase detection module 810 can also output a gait signal conveying information about the user's gait, such as the current phase of the gait (e.g., heel strike, toe off, stance phase), average duration of phases of the gait, expected time of the next change in phase of the gait, or other such information.

Figure 9:
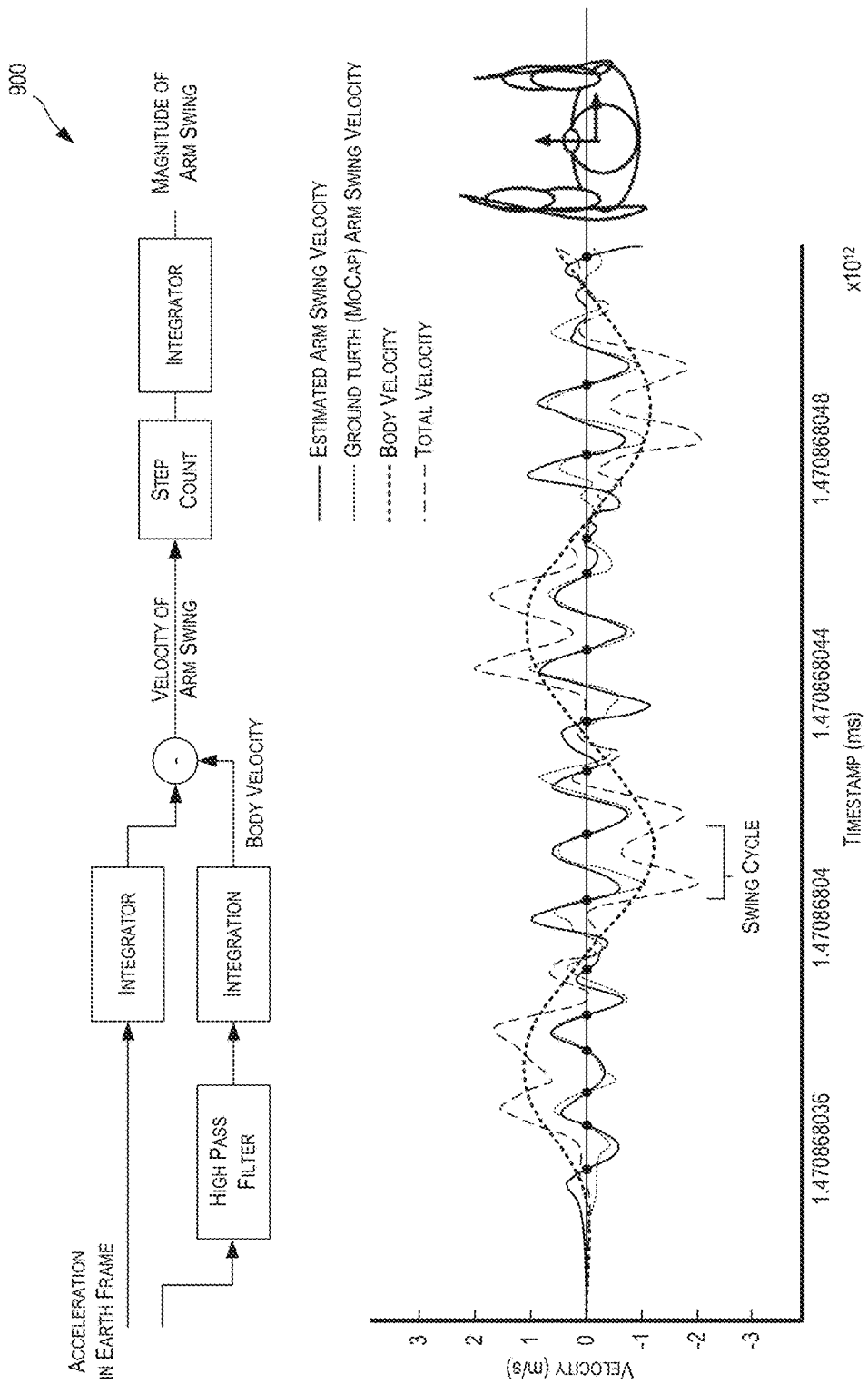
FIG. 9 is a combination schematic diagram and velocity chart depicting a system for determining arm swing magnitude using a wrist-worn sensor, according to certain aspects of the present disclosure.

FIG. 9 is a combination schematic diagram and velocity chart depicting a system 900 for determining arm swing magnitude using a wrist-worn sensor, according to certain aspects of the present disclosure. In this example, arm swing magnitude and upper limb movement asymmetry can be used to assess Parkinson's disease stages in general. Further, freezing episodes in upper limbs can be correlated with the freezing of gait severity.

To isolate the arm swing movement from the body movement, first a high pass filter can be applied to remove low frequency signals from the acceleration data in the global frame, as such signals are mainly contributed to by upper body movement during walking. Next, arm swing direction can be determined by calculating the principal component of the X-Y components of the resulting acceleration within short time intervals (e.g., at or approximately every 2 seconds). Finally, the arm swing magnitude can be calculated by integration within each arm swing cycle.

Figure 10:
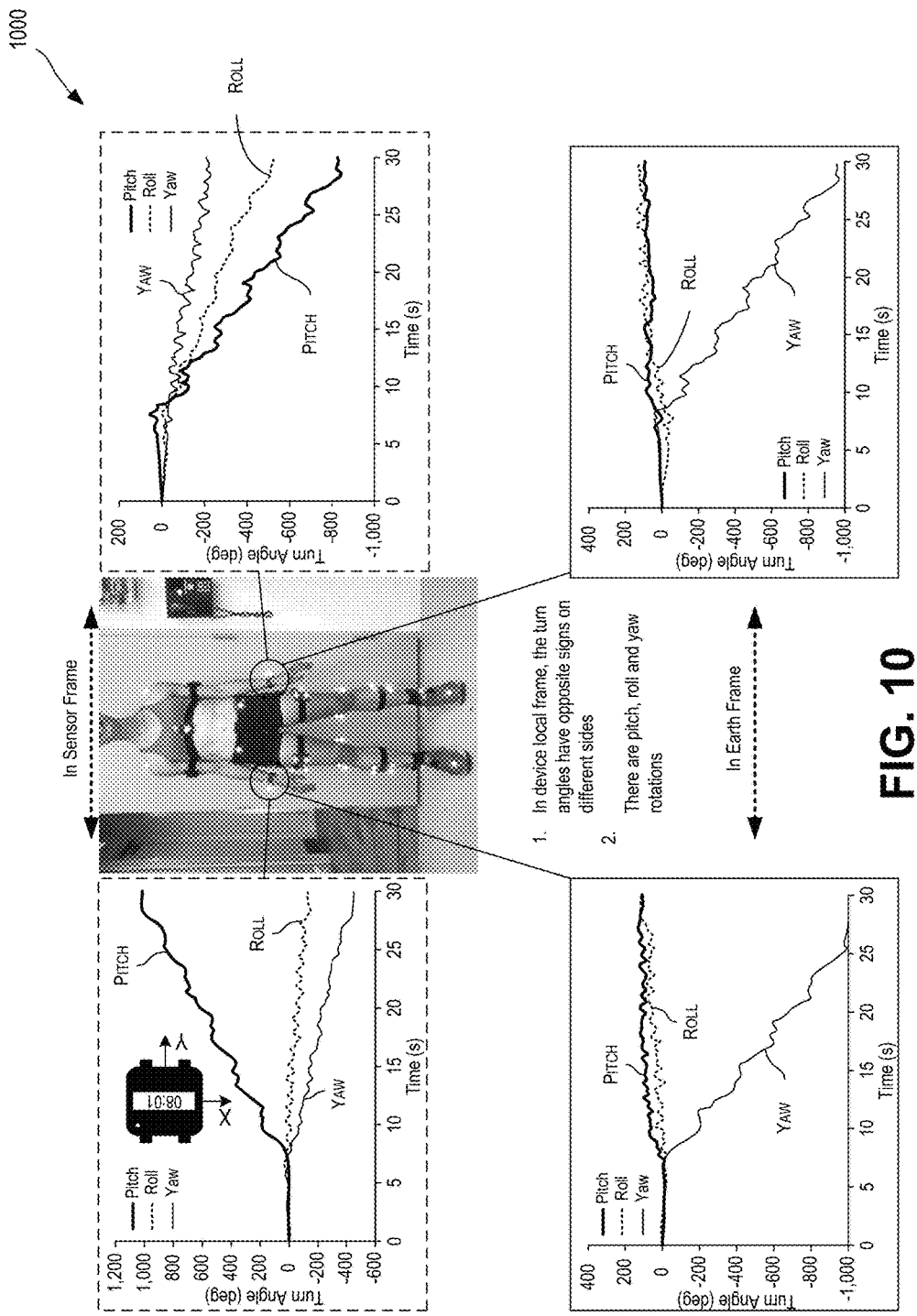
FIG. 10 is a set of charts depicting sensor data in the sensor frame and movement data in the global frame for a set of two wrist-worn sensors positioned on opposite arms according to certain aspects of the disclosure.

FIG. 10 is a set of charts 1000 depicting sensor data in the sensor frame and movement data in the global frame for a set of two wrist-worn sensors positioned on opposite arms according to certain aspects of the disclosure. As depicted in FIG. 10, the top two charts depict sensor data in the sensor frame and the bottom two charts depict movement data in the global frame as transformed from the respective sensor data according to certain aspects and features of the present disclosure. As depicted in FIG. 10, the leftmost charts are associated with a sensor on the user's right wrist and the rightmost charts are associated with a sensor on the user's left wrist. The charts 1000 show that despite obvious differences in the sensor data generated by the left and right sensors, the movement data resulting from the respective sensor data is nearly identical.

Figure 11:
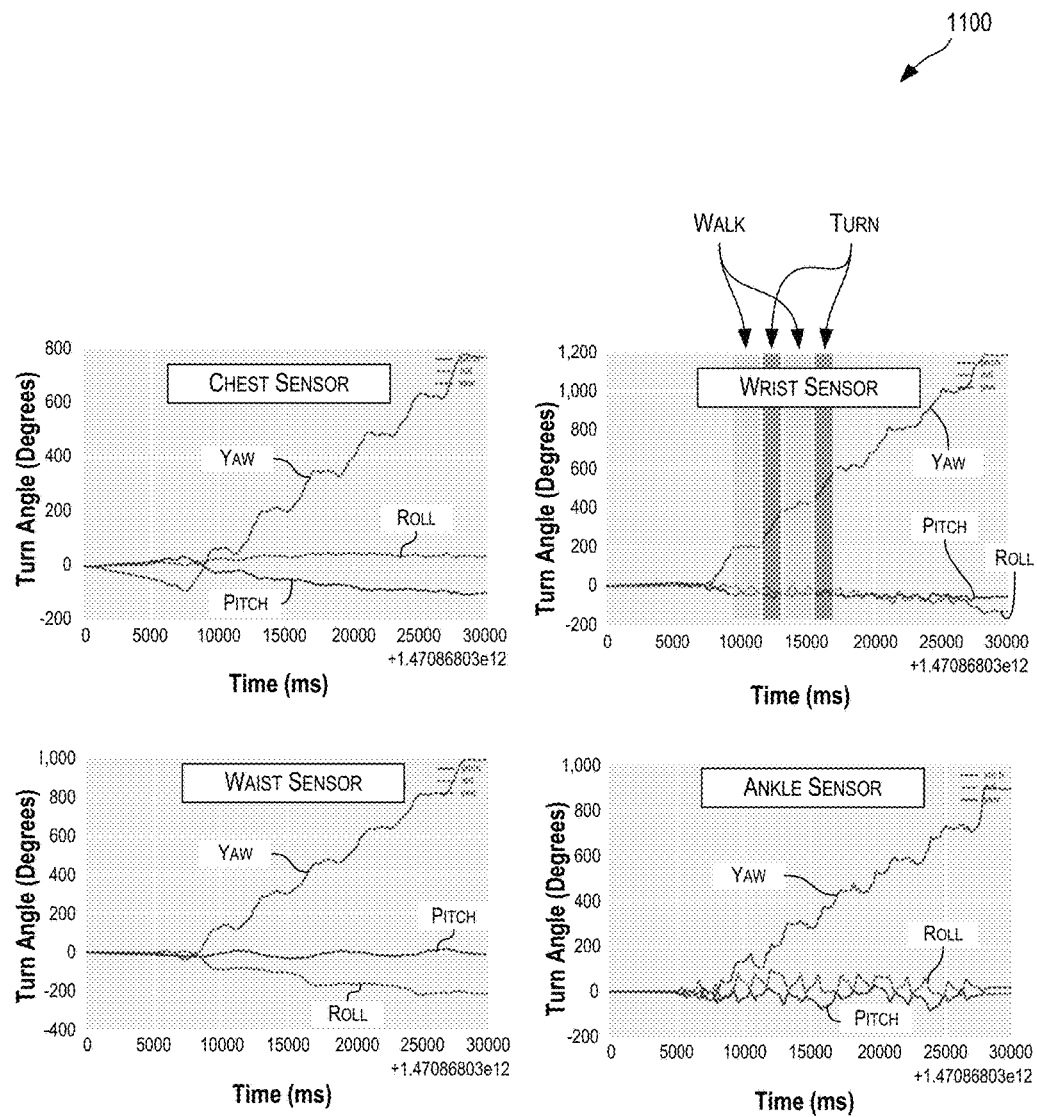
FIG. 11 is a set of charts depicting cumulative turn angles in the global frame as detected via sensors placed at varying locations on a user according to certain aspects of the present disclosure.

FIG. 11 is a set of charts 1100 depicting cumulative turn angles in the global frame as detected via sensors placed at varying locations on a user according to certain aspects of the present disclosure. A cumulative turn angle can be the total amount of rotation incurred by a user while walking back and forth several times. As seen in FIG. 11, the user always turned in the same direction (e.g., clockwise or counterclockwise) before continuing walking. From the top-left of FIG. 11 and continuing clockwise, the charts depict cumulative turn angles for i) a chest-worn sensor, ii) a wrist-worn sensor, iii) a waist-worn sensor, and iv) an ankle worn sensor. The cumulative turn angles are derived from yaw data in the global frame, similarly to the cumulative turn angles described with reference to FIGS. 2 and 3. The charts 1100 clearly show that once in the global frame, the biomechanical features (e.g., turn angles) discernable from the movement data can be sensor-location-agnostic (e.g., the location of the sensor does not substantially affect the ability to discern or otherwise monitor the biomechanical feature).

In some cases, a system can extracting activity metrics and gait features according to certain aspects of the present disclosure. Raw sensor data can be collected from sensor(s), such as a wrist sensor and an ankle sensor. The sensor data can be analyzed by an activity classifier which can determine what acitvity is occuring based on the received sensor data. In some cases, the activity classifier can also access additional third data, such as pulse analysis data indicative of pulse rate variability.

In some cases, the activity classifier can use sensor data from a first sensor (e.g., wrist sensor) or additional data source (e.g., pulse rate variability) to determine when a user is active or idle. This active or idle determination can then be applied to the sensor data from a second sensor (e.g., ankle sensor) to provide further insight into how to classify the sensor data from the second sensor. For example, the gait analysis of the sensor data from the ankle sensor can be facilitated by the active/idle determination of the activity classifier.

Various aspects and features of the present disclosure may be used individually or jointly. Further, certain aspects and features of the present disclosure can be utilized in any number of environments and applications beyond those described herein without departing from the broader spirit and scope of the specification. The specification and drawings are, accordingly, to be regarded as illustrative.

In the foregoing description, for the purposes of illustration, methods were described in a particular order. It should be appreciated that in alternate embodiments, the methods may be performed in a different order than that described. The methods described above may be performed by hardware components or may be embodied in sequences of machine-executable instructions, which may be used to cause a machine, such as a general-purpose or special-purpose processor or logic circuits programmed with the instructions to perform the methods (e.g., an ASIC). These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Where components are described as being configured to perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

As used below, any reference to a series of examples is to be understood as a reference to each of those examples disjunctively (e.g., "Examples 1-4" is to be understood as "Examples 1, 2, 3, or 4").

Example 1 is a system, comprising: one or more data processors; and a non-transitory computer-readable storage medium containing instructions which, when executed on the one or more data processors, cause the one or more data processors to perform operations including: receiving sensor data in a sensor frame, wherein the sensor data is indiactive of movement of a wearable device; identifying a reference event using at least a portion of the sensor data; determining a reference sensor orientation at the reference event using at least the portion of the sensor data, wherein the reference sensor orientation is associated with an orientation of the wearable device in a global frame; calculating a transformation parameter using the reference sensor orientation and the sensor data, wherein the transformation parameter includes a quaternion or a rotational matrix; transforming the sensor data using the transformation parameter to generate movement data, wherein the movement data is associated with movement of the wearable device in the global frame; and determining a sensor-location-agnostic biomechanical feature using the movement data. In some cases, identifying the reference event occurs automatically.

Example 2 is the system of example 1, wherein the sensor-location-agnostic biomechanical feature is associated with movement of a body part at which the wearable device is not positioned.

Example 3 is the system of examples 1 or 2, wherein the operations further comprise: receiving supplemental sensor data associated with continued movement of the wearable device in the sensor frame; transforming the supplemental sensor data using the transformation parameter to generate supplemental movement data, wherein the supplemental movement data is associated with continued movement of the wearable device in the global frame; and determining the sensor-location-agnostic biomechanical feature using the movement data.

Example 4 is the system of example 3, wherein the operations further comprise: automatically identifying a supplemental reference event using at least some of the supplemental sensor data; determining a supplemental reference sensor orientation at the supplemental reference event using at least the portion of the supplemental sensor data, wherein the supplemental reference sensor orientation is associated with a supplemental orientation of the wearable device in the global frame; and updating the transformation parameter using the supplemental reference sensor orientation and the supplemental sensor data, wherein transforming the supplemental sensor data using the transformation parameter to generate supplemental movement data includes using the updated transformation parameter.

Example 5 is the system of examples 1-4, wherein the operations further comprise: determining that the wearable device is being worn again after being removed from an original location; receiving new sensor data associated with movement of the wearable device in a new sensor frame, wherein the new sensor data is associated with movement of the wearable device being worn at a new location that is different from the original location; automatically identifying a new reference event using at least a portion of the new sensor data; determining a new reference sensor orientation at the new reference event using at least the portion of the new sensor data, wherein the new reference sensor orientation is associated with the orientation of the wearable device in the global frame; calculating a new transformation parameter using the new reference sensor orientation and the new sensor data, wherein the new transformation parameter includes a quaternion or a rotational matrix; transforming the new sensor data using the new transformation parameter to generate new movement data, wherein the new movement data is associated with movement of the wearable device in the global frame; and determining the sensor-location-agnostic biomechanical feature using the new movement data.

Example 6 is the system of examples 1-5, wherein the operations further comprise generating a diagnosis inference using the sensor-location-agnostic biomechanical feature.

Example 7 is the system of examples 1-6, wherein the operations further comprise receiving second movement data associated with movement of a second wearable device in the global frame, wherein the second wearable device is spaced apart from the wearable device, and wherein inferring the sensor-location-agnostic biomechanical feature includes using the movement data and the second movement data.

Example 8 is the system of examples 1-8, wherein determining the sensor-location-agnostic biomechanical feature includes: calculating a velocity of the sensor in the global frame using the re-oriented movement data; detecting an occurrence of a zero-expected-velocity event using the sensor data; calculating an offset between zero and the calculated velocity when the zero-expected-velocity event occurs; and correcting the calculated velocity using the offset.

Example 9 is a computer-implemented method, comprising: receiving sensor data in a sensor frame, wherein the sensor data is indicative of movement of a wearable device; automatically identifying a reference event using at least a portion of the sensor data; determining a reference sensor orientation at the reference event using at least the portion of the sensor data, wherein the reference sensor orientation is associated with an orientation of the wearable device in a global frame; calculating a transformation parameter using the reference sensor orientation and the sensor data, wherein the transformation parameter includes a quaternion or a rotational matrix; transforming the sensor data using the transformation parameter to generate movement data, wherein the movement data is associated with movement of the wearable device in the global frame; and determining a sensor-location-agnostic biomechanical feature using the movement data.

Example 10 is the method of example 9, wherein the sensor-location-agnostic biomechanical feature is associated with movement of a body part at which the wearable device is not positioned.

Example 11 is the method of examples 9 or 10, further comprising: receiving supplemental sensor data associated with continued movement of the wearable device in the sensor frame; transforming the supplemental sensor data using the transformation parameter to generate supplemental movement data, wherein the supplemental movement data is associated with continued movement of the wearable device in the global frame; and determining the sensor-location-agnostic biomechanical feature using the movement data.

Example 12 is the method of example 11, further comprising: automatically identifying a supplemental reference event using at least some of the supplemental sensor data; determining a supplemental reference sensor orientation at the supplemental reference event using at least the portion of the supplemental sensor data, wherein the supplemental reference sensor orientation is associated with a supplemental orientation of the wearable device in the global frame; and updating the transformation parameter using the supplemental reference sensor orientation and the supplemental sensor data, wherein transforming the supplemental sensor data using the transformation parameter to generate supplemental movement data includes using the updated transformation parameter.

Example 13 is the method of examples 9-12, further comprising: determining that the wearable device is being worn again after being removed from an original location; receiving new sensor data associated with movement of the wearable device in a new sensor frame, wherein the new sensor data is associated with movement of the wearable device being worn at a new location that is different from the original location; automatically identifying a new reference event using at least a portion of the new sensor data; determining a new reference sensor orientation at the new reference event using at least the portion of the new sensor data, wherein the new reference sensor orientation is associated with the orientation of the wearable device in the global frame; calculating a new transformation parameter using the new reference sensor orientation and the new sensor data, wherein the new transformation parameter includes a quaternion or a rotational matrix; transforming the new sensor data using the new transformation parameter to generate new movement data, wherein the new movement data is associated with movement of the wearable device in the global frame; and determining the sensor-location-agnostic biomechanical feature using the new movement data.

Example 14 is the method of examples 9-13, further comprising generating a diagnosis inference using the sensor-location-agnostic biomechanical feature.

Example 15 is the method of examples 9-14, further comprising receiving second movement data associated with movement of a second wearable device in the global frame, wherein the second wearable device is spaced apart from the wearable device, and wherein inferring the sensor-locationagnostic biomechanical feature includes using the movement data and the second movement data.

Example 16 is the method of examples 9-15, wherein determining the sensor-location-agnostic biomechanical feature includes: calculating a velocity of the sensor in the global frame using the re-oriented movement data; detecting an occurrence of a zero-expected-velocity event using the sensor data; calculating an offset between zero and the calculated velocity when the zero-expected-velocity event occurs; and correcting the calculated velocity using the offset.

Example 17 is a computer-program product tangibly embodied in a non-transitory machine-readable storage medium, including instructions configured to cause a data processing apparatus to perform operations including: receiving sensor data in a sensor frame, wherein the sensor data is indicative of movement of a wearable device; automatically identifying a reference event using at least a portion of the sensor data; determining a reference sensor orientation at the reference event using at least the portion of the sensor data, wherein the reference sensor orientation is associated with an orientation of the wearable device in a global frame; calculating a transformation parameter using the reference sensor orientation and the sensor data, wherein the transformation parameter includes a quaternion or a rotational matrix; transforming the sensor data using the transformation parameter to generate movement data, wherein the movement data is associated with movement of the wearable device in the global frame; and determining a sensor-location-agnostic biomechanical feature using the movement data.

Example 18 is the computer-program product of example 17, wherein the sensor-location-agnostic biomechanical feature is associated with movement of a body part at which the wearable device is not positioned.

Example 19 is the computer-program product of examples 17 or 18, wherein the operations further comprise: receiving supplemental sensor data associated with continued movement of the wearable device in the sensor frame; transforming the supplemental sensor data using the transformation parameter to generate supplemental movement data, wherein the supplemental movement data is associated with continued movement of the wearable device in the global frame; and determining the sensor-location-agnostic biomechanical feature using the movement data.

Example 20 is the computer-program product of example 19, wherein the operations further comprise: automatically identifying a supplemental reference event using at least some of the supplemental sensor data; determining a supplemental reference sensor orientation at the supplemental reference event using at least the portion of the supplemental sensor data, wherein the supplemental reference sensor orientation is associated with a supplemental orientation of the wearable device in the global frame; and updating the transformation parameter using the supplemental reference sensor orientation and the supplemental sensor data, wherein transforming the supplemental sensor data using the transformation parameter to generate supplemental movement data includes using the updated transformation parameter.

Example 21 is the computer-program product of examples 17-20, wherein the operations further comprise: determining that the wearable device is being worn again after being removed from an original location; receiving new sensor data associated with movement of the wearable device in a new sensor frame, wherein the new sensor data is associated with movement of the wearable device being worn at a new location that is different from the original location; automatically identifying a new reference event using at least a portion of the new sensor data; determining a new reference sensor orientation at the new reference event using at least the portion of the new sensor data, wherein the new reference sensor orientation is associated with the orientation of the wearable device in the global frame; calculating a new transformation parameter using the new reference sensor orientation and the new sensor data, wherein the new transformation parameter includes a quaternion or a rotational matrix; transforming the new sensor data using the new transformation parameter to generate new movement data, wherein the new movement data is associated with movement of the wearable device in the global frame; and determining the sensor-location-agnostic biomechanical feature using the new movement data.

Example 22 is the computer-program product of examples 17-21, wherein the operations further comprise generating a diagnosis inference using the sensor-location-agnostic biomechanical feature.

Example 23 is the computer-program product of examples 17-22, wherein the operations further comprise receiving second movement data associated with movement of a second wearable device in the global frame, wherein the second wearable device is spaced apart from the wearable device, and wherein inferring the sensor-location-agnostic biomechanical feature includes using the movement data and the second movement data.

Example 24 is the computer-program product of examples 17-23, wherein determining the sensor-location-agnostic biomechanical feature includes: calculating a velocity of the sensor in the global frame using the re-oriented movement data; detecting an occurrence of a zero-expected-velocity event using the sensor data; calculating an offset between zero and the calculated velocity when the zero-expected-velocity event occurs; and correcting the calculated velocity using the offset.

Example 25 is a method, comprising: receiving motion data relative to a sensor frame, wherein the motion data includes accelerometer data; determining a coordinate transformation function based on the motion data; transforming, using the coordinate transformation function, to convert the motion data into a global frame; detecting gait phase data based on the motion data; computing velocity data by integrating the converted motion data in the global frame; and calibrating the velocity data based on the detected gait phase data.

Example 26 is the method of example 25, wherein detecting the gait phase data includes identifying a foot fall event by analyzing the motion data, and wherein calibrating the velocity data is by adjusting a velocity offset parameter to match the foot fall event to a zero velocity value.

Example 27 is a system, comprising: one or more data processors; and a non-transitory computer-readable storage medium containing instructions which, when executed on the one or more data processors, cause the one or more data processors to perform operations including: receiving motion data relative to a sensor frame, wherein the motion data includes accelerometer data; determining a coordinate transformation function based on the motion data; transforming, using the coordinate transformation function, to convert the motion data into a global frame; detecting gait phase data based on the motion data; computing velocity data by integrating the converted motion data in the global frame; and calibrating the velocity data based on the detected gait phase data.

Example 28 is the system of example 27, wherein detecting the gait phase data includes identifying a foot fall event by analyzing the motion data, and wherein calibrating the velocity data is by adjusting a velocity offset parameter to match the foot fall event to a zero velocity value.

Example 29 is a computer-program product tangibly embodied in a non-transitory machine-readable storage medium, including instructions configured to cause a data processing apparatus to perform operations including: receiving motion data relative to a sensor frame, wherein the motion data includes accelerometer data; determining a coordinate transformation function based on the motion data; transforming, using the coordinate transformation function, to convert the motion data into a global frame; detecting gait phase data based on the motion data; computing velocity data by integrating the converted motion data in the global frame; and calibrating the velocity data based on the detected gait phase data.

Example 30 is the system of example 29, wherein detecting the gait phase data includes identifying a foot fall event by analyzing the motion data, and wherein calibrating the velocity data is by adjusting a velocity offset parameter to match the foot fall event to a zero velocity value.

What is claimed is:

1. A system, comprising:
   one or more data processors; and
   a non-transitory computer-readable storage medium containing instructions which, when executed on the one or more data processors, cause the one or more data processors to perform operations including:
      receiving sensor data in a sensor frame, wherein the sensor data is indicative of movement of a wearable device that is location-agnostic to a biomechanical feature of a user;
      dynamically identifying a reference event using at least a portion of the sensor data, wherein dynamically identifying the reference event includes analyzing at least the portion of the sensor data to detect aspects of the sensor data associated with the reference event;
      determining a reference sensor orientation during the reference event using at least the portion of the sensor data, wherein the reference sensor orientation is associated with an orientation of the wearable device in a global frame;
      calculating a transformation parameter using the reference sensor orientation and the sensor data, wherein the transformation parameter includes a quaternion or a rotational matrix;
      transforming the sensor data using the transformation parameter to generate re-oriented movement data, wherein the re-oriented movement data is associated with movement of the wearable device in the global frame; and
      determining the biomechanical feature using the re-oriented movement data, wherein determining the biomechanical feature occurs irrespective of placement of the wearable device on the user.

2. The system of claim 1, wherein the biomechanical feature is associated with movement of a body part at which the wearable device is not positioned.

3. The system of claim 1, wherein the operations further comprise:
   receiving supplemental sensor data associated with continued movement of the wearable device in the sensor frame;
   transforming the supplemental sensor data using the transformation parameter to generate supplemental re-oriented movement data, wherein the supplemental re-oriented movement data is associated with continued movement of the wearable device in the global frame; and
   determining the biomechanical feature using the supplemental re-oriented movement data.

4. The system of claim 3, wherein the operations further comprise:
   automatically identifying a supplemental reference event using at least some of the supplemental sensor data;
   determining a supplemental reference sensor orientation at the supplemental reference event using at least the portion of the supplemental sensor data, wherein the supplemental reference sensor orientation is associated with a supplemental orientation of the wearable device in the global frame; and
   updating the transformation parameter using the supplemental reference sensor orientation and the supplemental sensor data, wherein transforming the supplemental sensor data using the transformation parameter to generate supplemental re-oriented movement data includes using the updated transformation parameter.

5. The system of claim 1, wherein the operations further comprise:
   determining that the wearable device is being worn again after being removed from an original location;
   receiving new sensor data associated with movement of the wearable device in a new sensor frame, wherein the new sensor data is associated with movement of the wearable device being worn at a new location that is different from the original location;
   automatically identifying a new reference event using at least a portion of the new sensor data;
   determining a new reference sensor orientation at the new reference event using at least the portion of the new sensor data, wherein the new reference sensor orientation is associated with the orientation of the wearable device in the global frame;
   calculating a new transformation parameter using the new reference sensor orientation and the new sensor data, wherein the new transformation parameter includes a quaternion or a rotational matrix;
   transforming the new sensor data using the new transformation parameter to generate new re-oriented movement data, wherein the new re-oriented movement data is associated with movement of the wearable device in the global frame; and
   determining the biomechanical feature using the new re-oriented movement data.

6. The system of claim 1, wherein the operations further comprise generating a diagnosis inference using the biomechanical feature.

7. The system of claim 1, wherein the operations further comprise receiving second movement data associated with movement of a second wearable device in the global frame, wherein the second wearable device is spaced apart from the wearable device, and wherein inferring the biomechanical feature includes using the re-oriented movement data and the second movement data.

8. The system of claim 1, wherein determining the sensor-location-agnostic biomechanical feature includes:
   calculating a velocity of the sensor in the global frame using the re-oriented movement data;
   detecting an occurrence of a zero-expected-velocity event using the sensor data;

calculating an offset between zero and the calculated velocity when the zero-expected-velocity event occurs; and correcting the calculated velocity using the offset.

9. A computer-implemented method, comprising:

receiving sensor data in a sensor frame, wherein the sensor data is indicative of movement of a wearable device that is location-agnostic to a biomechanical feature of a user;

dynamically identifying a reference event using at least a portion of the sensor data, wherein dynamically identifying the reference event includes analyzing at least the portion of the sensor data to detect aspects of the sensor data associated with the reference event;

determining a reference sensor orientation during the reference event using at least the portion of the sensor data, wherein the reference sensor orientation is associated with an orientation of the wearable device in a global frame;

calculating a transformation parameter using the reference sensor orientation and the sensor data, wherein the transformation parameter includes a quaternion or a rotational matrix;

transforming the sensor data using the transformation parameter to generate re-oriented movement data, wherein the re-oriented movement data is associated with movement of the wearable device in the global frame; and determining the biomechanical feature using the re-oriented movement data, wherein determining the biomechanical feature occurs irrespective of placement of the wearable device on the user.

10. The method of claim 9, wherein the biomechanical feature is associated with movement of a body part at which the wearable device is not positioned.

11. The method of claim 9, further comprising:

receiving supplemental sensor data associated with continued movement of the wearable device in the sensor frame;

transforming the supplemental sensor data using the transformation parameter to generate supplemental re-oriented movement data, wherein the supplemental re-oriented movement data is associated with continued movement of the wearable device in the global frame; and determining the biomechanical feature using the supplemental re-oriented movement data.

12. The method of claim 11, further comprising:

automatically identifying a supplemental reference event using at least some of the supplemental sensor data;

determining a supplemental reference sensor orientation at the supplemental reference event using at least the portion of the supplemental sensor data, wherein the supplemental reference sensor orientation is associated with a supplemental orientation of the wearable device in the global frame; and updating the transformation parameter using the supplemental reference sensor orientation and the supplemental sensor data, wherein transforming the supplemental sensor data using the transformation parameter to generate supplemental re-oriented movement data includes using the updated transformation parameter.

13. The method of claim 9, further comprising:

determining that the wearable device is being worn again after being removed from an original location;

receiving new sensor data associated with movement of the wearable device in a new sensor frame, wherein the new sensor data is associated with movement of the wearable device being worn at a new location that is different from the original location;

automatically identifying a new reference event using at least a portion of the new sensor data;

determining a new reference sensor orientation at the new reference event using at least the portion of the new sensor data, wherein the new reference sensor orientation is associated with the orientation of the wearable device in the global frame;

calculating a new transformation parameter using the new reference sensor orientation and the new sensor data, wherein the new transformation parameter includes a quaternion or a rotational matrix;

transforming the new sensor data using the new transformation parameter to generate new re-oriented movement data, wherein the new re-oriented movement data is associated with movement of the wearable device in the global frame; and determining the biomechanical feature using the new re-oriented movement data.

14. The method of claim 9, further comprising generating a diagnosis inference using the biomechanical feature.

15. The method of claim 9, further comprising receiving second movement data associated with movement of a second wearable device in the global frame, wherein the second wearable device is spaced apart from the wearable device, and wherein inferring the biomechanical feature includes using the movement data and the second movement data.

16. The method of claim 9, wherein determining the sensor-location-agnostic biomechanical feature includes:

calculating a velocity of the sensor in the global frame using the re-oriented movement data;

detecting an occurrence of a zero-expected-velocity event using the sensor data;

calculating an offset between zero and the calculated velocity when the zero-expected-velocity event occurs; and correcting the calculated velocity using the offset.

17. A computer-program product tangibly embodied in a non-transitory machine-readable storage medium, including instructions configured to cause a data processing apparatus to perform operations including:

receiving sensor data in a sensor frame, wherein the sensor data is indicative of movement of a wearable device that is location-agnostic to a biomechanical feature of a user;

dynamically identifying a reference event using at least a portion of the sensor data, wherein dynamically identifying the reference event includes analyzing at least the portion of the sensor data to detect aspects of the sensor data associated with the reference event;

determining a reference sensor orientation during the reference event using at least the portion of the sensor data, wherein the reference sensor orientation is associated with an orientation of the wearable device in a global frame;

calculating a transformation parameter using the reference sensor orientation and the sensor data, wherein the transformation parameter includes a quaternion or a rotational matrix;

transforming the sensor data using the transformation parameter to generate re-oriented movement data, wherein the re-oriented movement data is associated with movement of the wearable device in the global frame; and determining a the biomechanical feature using the re-oriented movement data, wherein determining the biomechanical feature occurs irrespective of placement of the wearable device on the user.

18. The computer-program product of claim 17, wherein the biomechanical feature is associated with movement of a body part at which the wearable device is not positioned.

19. The computer-program product of claim 17, wherein the operations further comprise:
receiving supplemental sensor data associated with continued movement of the wearable device in the sensor frame;
transforming the supplemental sensor data using the transformation parameter to generate supplemental re-oriented movement data, wherein the supplemental re-oriented movement data is associated with continued movement of the wearable device in the global frame; and
determining the biomechanical feature using the supplemental re-oriented movement data.

20. The computer-program product of claim 19, wherein the operations further comprise:
automatically identifying a supplemental reference event using at least some of the supplemental sensor data;
determining a supplemental reference sensor orientation at the supplemental reference event using at least the portion of the supplemental sensor data, wherein the supplemental reference sensor orientation is associated with a supplemental orientation of the wearable device in the global frame; and
updating the transformation parameter using the supplemental reference sensor orientation and the supplemental sensor data, wherein transforming the supplemental sensor data using the transformation parameter to generate supplemental re-oriented movement data includes using the updated transformation parameter.

21. The computer-program product of claim 17, wherein the operations further comprise:
determining that the wearable device is being worn again after being removed from an original location;
receiving new sensor data associated with movement of the wearable device in a new sensor frame, wherein the new sensor data is associated with movement of the wearable device being worn at a new location that is different from the original location;
automatically identifying a new reference event using at least a portion of the new sensor data;
determining a new reference sensor orientation at the new reference event using at least the portion of the new sensor data, wherein the new reference sensor orientation is associated with the orientation of the wearable device in the global frame;
calculating a new transformation parameter using the new reference sensor orientation and the new sensor data, wherein the new transformation parameter includes a quaternion or a rotational matrix;
transforming the new sensor data using the new transformation parameter to generate new re-oriented movement data, wherein the new re-oriented movement data is associated with movement of the wearable device in the global frame; and
determining the biomechanical feature using the new re-oriented movement data.

22. The computer-program product of claim 17, wherein the operations further comprise generating a diagnosis inference using the biomechanical feature.

23. The computer-program product of claim 17, wherein the operations further comprise receiving second movement data associated with movement of a second wearable device in the global frame, wherein the second wearable device is spaced apart from the wearable device, and wherein inferring the biomechanical feature includes using the movement data and the second movement data.

24. The computer-program product of claim 17, wherein determining the sensor-location-agnostic biomechanical feature includes:
calculating a velocity of the sensor in the global frame using the re-oriented movement data;
detecting an occurrence of a zero-expected-velocity event using the sensor data;
calculating an offset between zero and the calculated velocity when the zero-expected-velocity event occurs; and
correcting the calculated velocity using the offset.

25. A method, comprising:
receiving motion data relative to a sensor frame, wherein the motion data includes accelerometer data associated with a wearable device;
determining a coordinate transformation function based on the motion data, wherein determining the coordinate transformation function includes dynamically identifying a reference event using at least a portion of the motion data, wherein dynamically identifying the reference event includes analyzing the motion data to detect aspects of the motion data associated with the reference event, and wherein determining the coordinate transformation function includes using the identified reference event;
transforming, using the coordinate transformation function, to convert the motion data into a global frame;
detecting gait phase data based on the motion data;
computing velocity data by integrating the converted motion data in the global frame; and
calibrating the velocity data based on the detected gait phase data, wherein the calibrated velocity data is associated with velocity of the wearable device in the global frame irrespective of placement or orientation of the wearable device on a user.

26. The method of claim 25, wherein detecting the gait phase data includes identifying a foot fall event by analyzing the motion data, and wherein calibrating the velocity data is by adjusting a velocity offset parameter to match the foot fall event to a zero velocity value.

* * * * *